United States Patent
De Colle et al.

(10) Patent No.: US 11,147,820 B2
(45) Date of Patent: *Oct. 19, 2021

(54) METHODS FOR TREATING GI TRACT DISORDERS

(71) Applicant: Neurogastrx, Inc., Woburn, MA (US)

(72) Inventors: Cyril De Colle, Campbell, CA (US); Pankaj Pasricha, Ellicott City, MD (US)

(73) Assignee: NEUROGASTRX, INC., Woburn, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/862,762

(22) Filed: Apr. 30, 2020

(65) Prior Publication Data

US 2020/0281936 A1 Sep. 10, 2020

Related U.S. Application Data

(63) Continuation of application No. 16/216,257, filed on Dec. 11, 2018, now abandoned, which is a (Continued)

(51) Int. Cl.
*A61K 31/5415* (2006.01)
*A61K 45/06* (2006.01)
*A61K 31/198* (2006.01)
*A61K 31/197* (2006.01)
*C07D 417/06* (2006.01)

(52) U.S. Cl.
CPC ........ *A61K 31/5415* (2013.01); *A61K 31/197* (2013.01); *A61K 31/198* (2013.01); *A61K 45/06* (2013.01); *C07D 417/06* (2013.01)

(58) Field of Classification Search
CPC .................................................. A61K 31/5415
See application file for complete search history.

(56) References Cited

U.S. PATENT DOCUMENTS

| | | |
|---|---|---|
| 4,158,707 A | 6/1979 | Steffen et al. |
| 4,309,421 A | 1/1982 | Ghyczy et al. |

(Continued)

FOREIGN PATENT DOCUMENTS

| | | |
|---|---|---|
| CN | 102548555 A | 7/2012 |
| DE | 1092476 | 11/1960 |

(Continued)

OTHER PUBLICATIONS

Uezono, et al, "Gastrointestinal Motility Control Receptors Expressed in the Enteric Plexus and Gastrointestinal Function Improving Agents Targeting Such Receptors", Journal of Clinical and Experimental Medicine vol. 238 No. 10, pp. 904-908 Sep. 3, 2011 [with English Certification].

(Continued)

*Primary Examiner* — San Ming R Hui
(74) *Attorney, Agent, or Firm* — White & Case LLP

(57) ABSTRACT

Provided herein are methods, compositions, and kits for the treatment of an enteric nervous system disorder. Such methods may comprise administering to a subject an effective amount of a phenothiazine compound, a peripherally restricted dopamine decarboxylase inhibitor, and/or a peripherally restricted dopamine D2 receptor antagonist that does not substantially inhibit hERG channels.

15 Claims, 2 Drawing Sheets

Related U.S. Application Data continuation of application No. 15/717,765, filed on Sep. 27, 2017, now abandoned, which is a continuation of application No. 14/820,885, filed on Aug. 7, 2015, now Pat. No. 9,808,467, which is a continuation of application No. 14/555,455, filed on Nov. 26, 2014, now Pat. No. 9,132,134, which is a continuation of application No. PCT/US2013/076733, filed on Dec. 19, 2013.

(60) Provisional application No. 61/745,734, filed on Dec. 24, 2012.

(56) References Cited

U.S. PATENT DOCUMENTS

| | | | |
|---|---|---|---|
| 4,412,999 | A | 11/1983 | Remy et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,710,570 | A | 12/1987 | Thien |
| 4,925,678 | A | 5/1990 | Ranney |
| 4,959,217 | A | 9/1990 | Sanders et al. |
| 4,992,445 | A | 2/1991 | Lawter et al. |
| 5,001,139 | A | 3/1991 | Lawter et al. |
| 5,023,252 | A | 6/1991 | Hseih |
| 5,164,386 | A | 11/1992 | Cereda et al. |
| 5,164,405 | A | 11/1992 | McFarlane et al. |
| 5,167,616 | A | 12/1992 | Haak et al. |
| 5,169,383 | A | 12/1992 | Gyory et al. |
| 5,225,182 | A | 7/1993 | Sharma |
| 5,244,925 | A | 9/1993 | Wretlind et al. |
| 5,246,935 | A | 9/1993 | Jeppesen et al. |
| 5,434,174 | A | 7/1995 | Gidda et al. |
| 5,674,205 | A | 10/1997 | Pasricha et al. |
| 6,184,209 | B1 | 2/2001 | Smith |
| 6,239,122 | B1 | 5/2001 | Steele |
| 6,274,549 | B1 | 8/2001 | Dyrberg et al. |
| 6,528,521 | B2 | 3/2003 | Ruff et al. |
| 7,122,198 | B1 | 10/2006 | Singh et al. |
| 7,358,271 | B2 | 4/2008 | Barbeau |
| 7,615,207 | B2 | 11/2009 | Lin |
| 7,930,033 | B2 | 4/2011 | Chen et al. |
| 7,960,429 | B2 | 6/2011 | Mangel |
| 8,095,218 | B2 | 1/2012 | Gross et al. |
| 8,329,009 | B2 | 12/2012 | Osipchuk et al. |
| 8,349,818 | B2 | 1/2013 | DeLuca et al. |
| 9,132,134 | B2 | 9/2015 | De Colle et al. |
| 9,808,467 | B2 | 11/2017 | De Colle et al. |
| 9,844,554 | B2 | 12/2017 | De Colle et al. |
| 2002/0164777 | A1 | 11/2002 | Kelly et al. |
| 2003/0031707 | A1 | 2/2003 | Rubin |
| 2003/0176421 | A1 | 9/2003 | Watson et al. |
| 2005/0004155 | A1 | 1/2005 | Boyd et al. |
| 2005/0203185 | A1 | 9/2005 | Remenar et al. |
| 2006/0217391 | A1 | 9/2006 | Landau |
| 2006/0258732 | A1 | 11/2006 | Dinan et al. |
| 2006/0287221 | A1 | 12/2006 | Knudsen et al. |
| 2007/0129307 | A1 | 6/2007 | Tan et al. |
| 2009/0042871 | A1 | 2/2009 | Coats et al. |
| 2009/0054319 | A1 | 2/2009 | Talley et al. |
| 2009/0253634 | A1 | 10/2009 | Currie et al. |
| 2009/0326004 | A1 | 12/2009 | Kumar et al. |
| 2011/0282411 | A1 | 11/2011 | Knudson et al. |
| 2011/0319343 | A1 | 12/2011 | Shailubhai |
| 2012/0010228 | A1 | 1/2012 | Luehr et al. |
| 2012/0053121 | A1 | 3/2012 | Besner et al. |
| 2012/0077745 | A1 | 3/2012 | Polvino |
| 2012/0101089 | A1 | 4/2012 | Agarwal et al. |
| 2012/0115910 | A1 | 5/2012 | Seeman |
| 2012/0164139 | A1 | 6/2012 | Pasricha et al. |
| 2012/0283411 | A9 | 11/2012 | Currie et al. |
| 2018/0200258 | A1 | 7/2018 | De Colle et al. |
| 2019/0314384 | A1 | 10/2019 | De Colle et al. |
| 2020/0281936 | A1 | 9/2020 | Yu |

FOREIGN PATENT DOCUMENTS

| | | |
|---|---|---|
| DE | 2235998 A1 | 2/1973 |
| EP | 2581085 A1 | 4/2013 |
| FR | 2845914 A1 | 4/2004 |
| IN | 360/CHE/2010 | 8/2011 |
| IN | 2528/MUM/2013 | 6/2015 |
| WO | WO-2004082667 A1 | 9/2004 |
| WO | WO-2008134540 A1 | 11/2008 |
| WO | WO-2011107653 A1 | 9/2011 |
| WO | WO-2013028909 A1 | 2/2013 |
| WO | WO-2014105655 | 7/2014 |
| WO | WO-2015200369 A1 | 12/2015 |

OTHER PUBLICATIONS

U.S. Appl. No. 16/838,402, filed Apr. 2, 2020, Yu.

Abell, et al. "Treatment of gastroparesis: a multidisciplinary clinical review," Neurogastroenterol Motil., 2006, 18, 263-283.

Acosta, et al. "Prokinetics in gastroparesis," Gastroenterol Clin North Am. Mar. 2015;44(I):97-111. doi: 10.1016/j.gtc.2014.11.008. Epub Dec. 23, 2014.

Agrawal, et al., "University of Miami Division of Clinical Pharmacology Therapeutic Rounds: Update on Diagnosis and Treatment of Gastroparesis," American Journal of Therapeutics, Lippincott Williams & Wilkins, US, vol. 6, No. 2: 97-109, Mar. 1, 1999.

Angelo, et al., "High-performance liquid chromatographic method with fluorescence detection for the simultaneous determination of metopimazine and its acid metabolite in serum," J Chromatogr. Nov. 24, 1989;496(2):472-7.

Arbus, et al., "Use of metopimazine in certain vomitings from central origin," Therapeutique. May 1971;47(5):469-71.

Arnaud, et al., "Value of metopimazine (Vogalene) in the prevention and treatment of postoperative vomiting in ocular surgery. (Apropos of 100 cases)," Arch Ophtalmol Rev Gen Ophtalmol. Jan. 1972;32(I):63-8.

Babar, I. et al., "Gastroparesis Patient Treatment Survey, Survey 17-190," GuidePoint, pp. 1-18, May 26, 2017.

Badji, et al., "Comparative study of the effects of metoclopramide and metopimazine on the duodenojejunal motility during the interdigestive period: a manometric study in healthy subjects," Ann Gastroenterol Hepatol (Paris). Dec. 1988;24(7):369-74. [with Certified English Translation].

Ballestar, et al., "Clinical study of metopimazine in gastroenterology," Rev Esp Enferm Apar Dig. Jul. 1980;58(I):41-6. (with Machine Translation of Introduction).

Barale, et al., "Comparative study of the intestinal spasmolytic properties of metoclopramide and metopimazine," Anesth Analg (Paris). Jan.-Feb. 1977;34(1):47-54.

Berga, et al., "Comparison of clebopride, domperidone, metopimazine, and trimebutine as antiemetics and inducers of gastrointestinal peristalsis," Arch Farmacol Toxicol. Apr. 1981;7(1): 189-92. (with Machine Translation).

Berry, et al., "The prevention of radiation sickness. Report of a double blind random clinical trial using prochlorperazine and metopimazine," Clin Radiol. Oct. 1971;22(4):534-7.

Bertrand, et al., "Action of metopimazine on gastric motility. Double-blind study using external digestive electromyography," Nouv Presse Med. Oct. 4, 1975;4(32):2319-20. [with Certified English Translation].

Bethune-Volters, et al., "A randomized, double-blind trial assessing the efficacy and safety of sublingual metopimazine and ondansetron in the prophylaxis of chemotherapy-induced delayed emesis", Anti-Cancer Drugs, vol. 12(2): 217-224 (2006).

Blanes, et al., "Comparative study "in vitro" of transdermal absorption of a series of antiemetic drugs," Eur J Drug Metab Pharmacokinet. 1991;Spec No. 3:410-4.

Bloch, et al., "Comparison of the efficacy and safety of combinations of metopimazine or ondansetron with methylprednisolone in

(56) References Cited

OTHER PUBLICATIONS the prevention of delayed emesis in patients receiving chemotherapy," Curr Med Res Opin. Nov. 2005;21(11): 1763-71.
Bounoure, et al., "Effect of iontophoresis and penetration enhancers on transdermal absorption of metopimazine," J Dermatol Sci. Dec. 2008;52(3): 170-7. doi:10.1016/j.jdermsci.2008.06.009. Epub Aug. 3, 2008.
Camilleri, et al., "Clinical guideline: management of gastroparesis," Am J Gastroenterol. Jan. 2013;108:18-37; quiz 38. doi: 10.1038/ajg.2012.373. Epub Nov. 13, 2012.
Camilleri, "Clinical practice. Diabetic gastroparesis," N Engl J Med. Feb. 22, 2007;356(8):820-9.
Calpena, et al., "A comparative in vitro study of transdermal absorption of antiemetics," J Pharm Sci. Jan. 1994;83(1):29-33.
Casanova, et al., "A comparative study of alizapride and metopimazine," (author's transl). Sem Hop. Feb. 11, 1982;58(6):345-8.
Champion, "Management of idiopathic, diabetic and miscellaneous gastroparesis with cisapride," Scand J Gastroenterol Suppl. 165: 44-52; discussion 52-3 1989 abstract only.
Chu, et al., "A controlled clinical study of metopimazine and perphenazine in treatment of radiation nausea and vomiting," Clin Pharmacol Ther. Nov.-Dec. 1969;10(6):800-9.
Clavel, et al., "Improved control of emesis and quality of life with ondansetron in breast cancer," Oncology. May-Jun. 1993;50(3): 180-5.
Cournot, et al., "Antiemetic effect of metopimazine measured by the apomorphine test," Mar.-Apr. 1987;42(2): 183-6. (with English abstract).
Croom, et al., "Metopimazine a review of its use in the treatment of chemotherapy-induced nausea and vomiting," Am. J. Cancer. 2006; 5(2): 123-136.
Davis, et al., "A Systematic Review of the Treatment of Nausea and/or Vomiting in Cancer Unrelated to Chemotherapy or Radiation," vol. 39, No. 4. pp. 756-767 (2010).
Debray, et al., "Treatment of vomiting in infants and children induced by acute infectious pathology," A comparative study of alizapride versus metopimazine. Dec. 1990;37(10):683-7.
Des Varannes. Comments on the use of metopimazine in France. Attn. C. De Colle. Neurogastrx Inc. Jun. 16, 2015.
Diaz, et al., "The [$^3$H]dofetilide binding assay is a predictive screening tool for hERG blockade and proarrhythmia: Comparison of intact cell and membrane preparations and effects of altering [K$^+$]$_o$," J Pharmacol Toxicol Methods. Nov.-Dec. 2004;50(3): 187-99.
Djeddi, et al., "Effect of Domperidone on QT Interval in Neonates," The Journal of Pediatrics. 2008: 153(5):663-666.
Dorval, et al., "Dyspepsia: modern concept and therapeutic approaches," Gastro-Enterology, Jan. 14, 1989; 111(2):105-109 [with Certified English Translation].
Dupuis, et al., "Optimizing emetic control in children receiving antineoplastic therapy: beyond the guidelines," Pediatric Drugs. 2010; 12(1):51-61. doi: 10.2165/11316190-000000000-00000. Review.
Dupuis, et al., "Options for the prevention and management of acute chemo therapy-induced nausea and vomiting in children," Pediatric Drugs. 2003;5(9):597-613. Review.
Ellebaek, et al., "Optimizing antiemetic therapy in multiple-day and multiple cycles of chemotherapy," Curr Opin Support Palliat Care. Mar. 2008;2(I):28-34. doi: 10.1097/SPC.0b013e3282f44a75.
European search report and opinion dated May 13, 2016 for EP application No. 13869541.
Fedorak, et al., "A novel colon-specific steroid prodrug enhances sodium chloride absorption in rat colitis," Am J Physiol. Aug. 1995;269(2 Pt 1):G210-8.
Fieni, et al., "Clinical protocol for pregnancy termination in bitches using prostaglandin F2 alpha," J Reprod Fertil Suppl. 1997;51:245-50.
Frédéric, et al., "Percutaneous absorption of metopimazine and effect of cyclodextrins," Drug Dev Ind Pharm. May 2008;34(5):478-84. doi: 10.1080/03639040701743873.

Furness, "The enteric nervous system and neurogastroenterology," Nature Reviews Gastroenterology and Hepatol. 2012; 9:286-294.
Gaillot, et al., "Metabolic behavior of methopimazine as a function of route of administration. Impact of the first-pass effect on systemic bioavailability," Farmaco Prat. Jan. 1980;35(1):3-22.
Gazy, et al., "Differential pulse cathodic voltammetric determination of floctafenine and metopimazine," J Pharm Biomed Anal. Mar. 12, 2007;43(4): 1535-9. Epub Dec. 11, 2006.
Ghoos, et al., "Measurement of gastric emptying rate of solids by means of a carbon-labeled octanoic acid breath test," Gastroenterology. Jun. 1993;104(6):1640-7.
Gosselin, et al., "Manometric effects of metopimazine on the lower esophageal sphincter," (author's transl.). Sem Hop. Feb. 8-15, 1981;57(5-6):291-5. English abstract.
Guerin, et al., "Therapeutic value of metopimazine as an antiemetic in cancerology," Presse Med. May 17, 1969;77(24):893.
Hansen, "The enteric nervous system III: a target for pharmacological treatment," Pharmacol Toxicol. Jul. 2003;93: 1-13.
Harer, et al., "Chronic Unexplained Nausea and Vomiting or Gastric Neuromuscular Dysfunction (GND)? An Update on Nomenclature, Pathophysiology and Treatment, and Relationship to Gastroparesis," Current Treatment Options Gastroenterology. DO1 10.1007/s11938-016-0113-z, 12 pages, Oct. 8, 2016.
Hasler, "Symptomatic management for gastroparesis. Antiemetics, analgesics, and symptom modulators," Gastroenterol. Clin. N. Am. 2015; 44:113-126.
Herrstedt, et al., "Treatment of chemotherapy-induced nausea and vomiting," Ugeskr Laeger, Jan. 24, 1994, 156(4):453-460 Review. Danish with English summary on p. 459.
Herrstedt, et al., "Bioavailability of the antiemetic metopimazine given as a microenema," Br J Clin Pharmacol. Jun. 1996;41(6):613-5.
Herrstedt, et al., "Dose-finding study of oral metopimazine," Support Care Cancer. Jan. 1997;5:38-43.
Herrstedt, et al., "Interaction of the antiemetic metopimazine and anticancer agents with brain dopamine $D_2$, 5-hydroxytryptamine$_3$, histamine $H_1$, muscarine cholinergic and alpha$_1$-adrenergic receptors," Cancer Chemotherapy Pharmacology. 1993;33:53-6.
Herrstedt, et al., "Ondansetron plus metopimazine compared with ondansetron alone in patients receiving moderately emetogenic chemotherapy," N Engl J Med. Apr. 15, 1993;328(15):1076-80.
Herrstedt, et al., "Randomized, double-blind comparison of ondansetron versus ondansetron plus metopimazine as antiemetic prophylaxis during platinum-based chemotherapy in patients with cancer," J Clin Oncol. Apr. 1997; 15(4): 1690-6.
Herrstedt, et al., "Randomized, double-blind trial comparing the antiemetic effect of tropisetron plus metopimazine with tropisetron plus placebo in patients receiving multiple cycles of multiple-day cisplatin-based chemotherapy," Support Care Cancer. Apr. 2007;15(4):417-26. Epub Nov. 9, 2006.
Herrstedt, et al., "The effect of food on serum concentrations of metopimazine," Br J Clin Pharmacol. Aug. 1990;30(2):237-43.
Herrstedt, J. "Chemotherapy-induced nausea and vomiting with special emphasis on metopimazine," Dan Med Bull. Sep. 1998;45(4):412-22. Review.
Herrstedt, J. "Development of antiemetic therapy in cancer patients," Acta Oncol. 1995;34(5):637-40. Review.
Hershcovici, "Pharmacological management of GERD: where does it stand now?," Trends Pharmacol Sci. Apr. 2011;32(4):258-64.
Higuchi, et al., "Pro-drugs as novel drug delivery systems," American Chemical Society. ACS symposium series 14. 1975.
Hiyama, Toru et al., "Treatment of functional dyspepsia with serotonin agonists: A meta-analysis of randomized controlled trials," Journal of Gastroenterology and Hepatology, 22; 1566-1570 (2007).
Hochhaus, et al., "A selective HPLC/RIA for dexamethasone and its prodrug dexamethasone-21-sulphobenzoate sodium in biological fluids," Biomedical Chromatography. Nov.-Dec. 1992;6(6):283-6.
Hondeghem, "Domperidone: Limited Benefits With Significant Risk for Sudden Cardiac Death," Journal of Cardiovascular Pharmacology. 2013; 61(3):218-225.

(56) References Cited

OTHER PUBLICATIONS

Hubert-Roux, et al., "Fragmentation pathways of metopimazine and its metabolite using ESI-MS(n), HR-MS and H/D exchange," J Mass Spectrom. Oct. 2010;45(10): pp. 1121-1129. doi: 10.1002/jms.l790.

Huttunen, et al., "Pro-drugs—from serendipity to rational design," Pharmacol Rev. Sep. 2011; 63(3): pp. 750-771. doi: 10.1124/pr.110.003459. Epub Jul. 7, 2011.

International search report and written opinion dated May 21, 2014 for PCT/US2013/076733.

International Application No. PCT/US2015/037258 International Preliminary Report on Patentability dated Dec. 27, 2016.

Israel, et al., "Treatment of nausea and vomiting related to anticancerous multiple combination chemotherapy: results of two controlled studies," J Int Med Res. 1978;6(3):235-40.

Jadot, et al., "Comparative statistical study of two antiemetics, metoclopramide and metopimazine, effects on the oestrus cycle in the female rat," (author's transl). Pathol Biot (Paris). Jan. 1980;28(I):68-72. French with English Summary.

Janssen, et al., "The Relation Between Symptom Improvement and Gastric Emptying in the Treatment of Diabetic and Idiopathic Gastroparesis," The American Journal of Gastroenterology, vol. 108, Sep. 2013, pp. 1382-1391.

Jolliet, et al., "Evidence of lowest brain penetration of an antiemetic drug, metopimazine, compared to domperidone, metoclopramide and chlorpromazine, using an in vitro model of the blood-brain barrier," Pharmacol Res. Jul. 2007;56(I): pp. 11-17. Epub Dec. 19, 2006.

Khamales, et al., "A randomized, double-blind trial assessing the efficacy and safety of sublingual metopimazine and ondansetron in the prophylaxis of chemotherapy-induced delayed emesis," Anticancer Drugs. Feb. 2006;17(2):217-24. Erratum in: Anticancer Drugs. Jun. 2006;17(5):599.

Kilgore, et al., "Investigational use of metomidate hydrochloride as a shipping additive for two ornamental fishes," J Aquat Anim Health. Sep. 2009;21(3):133-9. doi: 10.1577/H08-030.1.

Knowles, et al., "New perspectives in the diagnosis and management of enteric neuropathies," Nature Reviews Gastroenterology and Hepatology. 2013; 10:206-218.

Larsen, et al., "Prodrug forms for the sulfonamide group. I. Evaluation of N-acyl derivatives, N-sulfonylamidines, N-sulfonylsulfilimines and sulfonylureas as possible prodrug derivatives," Int. J. Pharm. 1987; 37:87-95.

Larsen, et al., "Prodrug forms for the sulfonamide group. II. Water-soluble amino acid derivatives of N-methylsulfonamides as possible prodrugs," Int. J. Pharm. 1988; 47:103-110.

Laverdant, et al., "Functional manifestations of irritable bowel. Treatment by metopimazine. Manifestations fonctionnelles du colon irritable. Traiment para la metopimazine," Lyon Medical. Jan. 1, 1981; 245(4):183-185 (in French with English abstract).

Lebeau, et al., "The efficacy of a combination of ondansetron, methylprednisolone and metopimazine in patients previously uncontrolled with a dual antiemetic treatment in cisplatin-based chemotherapy," The French Ondansetron Study Group. Ann Oncol. Sep. 1997;8(9):887-92.

Li, et al., "Physiological modulation of intestinal motility by enteric dopaminergic neurons and the D2 receptor: analysis of dopamine receptor expression, location, development, and function in wild-type and knock-out mice," J Neurosci. Mar. 8, 2006;26(10):2798-807.

Llau, et al., "Drug-induced parkinsonian syndromes: a 10-year experience at a regional center of pharmaco-vigilance," Rev Neurol (Paris). Nov. 1994;150(11):757-62.

Mallet, et al., "Pharmacokinetic study of metopimazine by oral route in children," Pharmacology Research and Perspectives, vol. 3, Issue 3, pp. 1-7, 2015.

McLeod, et al., "A glucocorticoid prodrug facilitates normal mucosal function in rat colitis without adrenal suppression," Gastroenterology. Feb. 1994;106(2):405-13.

Metopimazine Label—Summary of Product Characteristics, dated Aug. 16, 2011 (agence-prd.ansm.sante.fr/php/ecodex/frames.php?specid=6831893l&typedoc=R&ref=R0195277.htm )(5 pages) [with Certified English Translation].

Merck. The Merck Index. Eleventh Ed. 1989. Monograph 4116 Fluphenazine. 655-656.

Monges, et al., "Clinical study of oral solution of Vogalene (metopimazine)," Etude clinique du solute buvable de Vogalene. Mediterranee Medicale. Jan. 1, 1975; 3(66):81-82 (in French with English machine translation).

Moertel, et al., "Controlled studies of metopimazine for the treatment of nausea and vomiting," J Clin Pharmacol. Jul. 1973;13(7):283-7.

Mozaffari, Shilan et al., "Metabolic and toxicological considerations for the latest drugs used to treat irritable bowel syndrome," Expert Opinion on Drug Metabolism & Toxicology, 9(4): 403-421 (2013).

Naguib, et al., "Development and validation of stability indicating HPLC and HPTLC methods for determination of sulpiride and mebeverine hydrochloride in combination," Eur JMedChem. Sep. 2010;45(9):3719-25. doi: 10.1016/j.ejmech.2010.05.021. Epub May 15, 2010.

Naguib, et al., "Stability indicating HPTLC method for determination of Metopimazine in pharmaceutical formulation and human plasma," Ben-Sue University Journal of Basic and Applied Science: 52-62 (2014).

Nathan, et al., "A pilot study of ondansetron plus metopimazine vs. ondansetron monotherapy in children receiving highly emetogenic chemotherapy: a Bayesian randomized serial N-of-1 trials design," Support Care Cancer. Mar. 2006;14(3):268-76. Epub Jul. 29, 2005.

Niemegeers, CJ., "Antiemetic specificity of dopamine antagonists," Psychopharmacology (Berl). 1982;78(3):210-3.

Nippon Naika Gakkai Zasshi, "Methods for Treating GI Tract Disorders," The Journal of the Japanese Society of Internal Medicine, vol. 2, pp. 122-127 (2006) [with Certified English Translation].

Norcliffe-Kaufmann, et al., "Hyperdopaminergic crises in familial dysautonomia: A randomized trial of carbidopa," Neurology. Apr. 23, 2013;80(17):1611-7. doi: 10.1212/WNL.0b013e31828fl8f0. Epub Apr. 3, 2013.

Obermayr, et al., "Development and developmental disorders of the enteric nervous system," Nature Reviews Gastroenterology and Hepatology. 2013; 10:43-57.

Ontario Health Technology Assessment Series, vol. 6, No. 16, p. 10 (2006).

Palfreyman, et al., "α-difluoromethyl DOPA, a new enzyme-activated irreversible inhibitor of aromatic L-amino acid decarboxylase," J Neurochem. Oct. 1978;31(4):927-32.

Paradis, et al., "A new antiemetic: The Vogalene (metopimazine or 9965 RP)," Laval Med. Dec. 1967;38(10):901-7. (machine translation).

Parkman, et al., "Gastroparesis and Functional Dyspepsia: Excerpts from the AGA/ANMS Meeting," Neurogastroenterol. Motil, Feb. 2010, 22(2): 113-133. doi:10.1111/j.1365-2982.2009.01434.x.

Parkman, et al, "Domperidone Treatment for Gastroparesis: Demographic and Pharmacogenetic Characterization of Clinical Efficacy and Side-Effects," Digestive Diseases and Sciences, Kluwer Academic Publishers-Plenum Publishers, NE, vol. 56, No. 1, pp. 115-124, Nov. 10, 2010.

Parkman, et al., "American Gastroenterological Association technical review on the diagnosis and treatment of gastroparesis," Gastroenterology. Nov. 2004; 127(5): 1592-622.

Parkman, et al., "Effect of nortriptyline on symptoms of idiopathic gastroparesis: the NORIG randomized clinical trial," JAMA. Dec. 25, 2013;310(24):2640-9. doi: 10.1001/jama.2013.282833.

Parrish, et al., "Nutrition Intervention for the Patient with Gastroparesis: An Update," Practical Gastroenterology. Aug. 2005; 29-66.

Pasricha, et al., "Toward a Better Drug for Gastroparesis: The Problem with a Moving Target," Gastroenterology, 2016, vol. 151, Issue 1, pp. 20-22.

Payne, et al., "Mechanisms of ligand binding and efficacy at the human D2(short) dopamine receptor," J Neurochem. Sep. 2002;82(5): 1106-17.

(56) References Cited

OTHER PUBLICATIONS

Pimentel, M. et al., "Low-Dose Nocturnal Tegaserod or Erythromycin Delays Symptom Recurrence After Treatment of Irritable Bowel Syndrome Based on presumed Bacterial Overgrowth," Gastroenterology & Hepatology 5(6);435-442 (Jun. 2009).
Priest, et al., "Role of hERG potassium channel assays in drug development," Channels (Austin). Mar.-Apr. 2008;2(2):87-93. Epub Mar. 5, 2008.
Quigley, Eamonn, "Prokinetics in the Management of Functional Gastrointestinal Disorders," Journal of Neurogastroenterology and Motility, 21(3); 330-336 (Jul. 2015).
Ray, K., "Motility: Mapping gastric dysrhythmias in gastroparesis—a slow wave of electrical activity," Nature Reviews Gastroenterology and Hepatology. 2012; 9:363.
Reddymasu, et al., "Pharmacotherapy of gastroparesis," Expert Opin Pharmacother. Feb. 2009;10(3):469-84.
Regina, et al., "Clinical tolerance of a new antidepressant—Milnacipran. L'Encephale". May-Jun. 1999;25(3):252-8. (English Abstract).
Rodary, et al., "Double blind randomized trial of metopimazine: for postoperative nausea and vomiting after cholecystectomy," Ann Anesthesiol Fr. 1979;20(2): 118-20.
Roila, et al., "Antiemetic effects of ondansetron and metopimazine," N Engl J Med. Oct. 28, 1993;329(18): 1356-7.
Sanguinetti, et al., "hERG potassium channels and cardiac arrhythmia," Nature. Mar. 23, 2006;440(7083):463-9.
Saphir, A., "Fighting nausea in the '90s: more and better antiemetics can help," J Natl Cancer Inst. Sep. 3, 1997;89(17):1252-5.
Seigneuric, et al., "Extrapyramidal syndrome. Possible role of metopimazine," Presse Med. Apr. 2, 1983;12(15):962-3.
Sigsgaard, et al., "Antiemetic efficacy of combination therapy with granisetron plus prednisolone plus the dopamine D2 antagonist metopimazine during multiple cycles of moderately emetogenic chemotherapy in patients refractory to previous antiemetic therapy," Support Care Cancer. May 2000;8(3):233-7.
Sigsgaard, et al., "Ondansetron plus metopimazine compared with ondansetron plus metopimazine plus prednisolone as antiemetic prophylaxis in patients receiving multiple cycles of moderately emetogenic chemotherapy," J Clin Oncol. Apr. 1, 2001; 19(7):2091-7.
Sigsgaard, et al., "Granisetron compared with prednisolone plus metopimazine as anti-emetic prophylaxis during multiple cycles of moderately emetogenic chemotherapy," Br J Cancer. May 1999;80(3-4):412-8.
Simmons, et al., "Granisetron transdermal system improves refractory nausea and vomiting in gastroparesis," Dig Dis Sci. Jun. 2014;59(6):1231-4. doi: 10.1007/s 10620-014-3097-3. Epub Mar. 11, 2014.
Sindelar, et al., "Modified Syntheses of 2-(Methylthio)-10-(2-(1-Methyl-2-Piperdinyl)Ethyl)Phenothiazine (Thioridazine) and 1-(3-(2-(Methylsulfonyl)-10-Phenothiazinyl)Propyl)-Piperidine-4-Carboxamide (Metopimazine)," Collect. Czech Chem Commun., vol. 55, pp. 1586-1601, 1990.
Sinkula, et al., "Rationale for design of biologically reversible drug derivatives: prodrugs," J Pharm Sci. Feb. 1975;64(2):181-210.
Stern, et al., "Electrogastrography: current issues in validation and methodology," Psychophysiology. Jan. 1987;24(1):55-64.
Stroyer, et al., "Clinical evaluation of an antiemetic, metopimazine (Vogalene) in an open and double-blind trial," Ugeskr Laeger. Jul. 12, 1976;138(29):1769-70. Danish with English Summary on p. 1770.
Thomforde, et al., "Evaluation of an inexpensive screening scintigraphic test of gastric emptying," JNucl Med. Jan. 1995;36(1):93-6.
Tonini, et al., "Effects of metopimazine on gastro-intestinal and biliary tract smooth muscle in vitro," Arch Int Pharmacodyn Ther. Jan. 1980;243(I): 139-148.
Tonini, et al., "Effects of metopimazine on motility of the gastrointestinal tract," Farmaco Prat. Oct. 1980;35(10):516-23.
Valeyre, et al., "Tolerance and efficacy of mefloquine as the first line treatment of uncomplicated *P. falciparum* malaria in children," Pathol Biol (Paris). Feb. 2008;56(I):21-8. doi: 10.1016/j.patbio. 2007.09.003. Epub Jan. 4, 2008. French.
Vallejo, et al., "Toxicity and dose response of intravenous (i.v.) metopimazine (MPZ) as preventive of high-dose cisplatin (CDDP)-induced emesis," Proc Am Soc Clin Oncol. 1988; 7:286.
Viala, et al., "A double-blind study of alizapride in nausea and emesis induced by cancer chemotherapeutic agents," (author's transl.). Sem Hop. Feb. 11, 1982 ;58(6):371-4.
European Medicines Agency, "Restrictions on the use of domperidone-containing medicines" Sep. 1, 2014, EMA/465179/2014, pp. 1-4.
European Medicines Agency, "European Medicines Agency recommends changes to the use of metoclopramide" Dec. 20, 2013, EMA/13239/2014 Corr. 1, pp. 1-5.
Metozolv ODT Label: Highlights of Prescribing Information; distributed by Salix Pharmaceuticals, Inc., 15 pages, 2010.
International Preliminary Report on Patentability dated Jun. 30, 2015 for International Application No. PCT/US2013/076733.
International Search Report and Written Opinion dated Nov. 24, 2015 for International Application No. PCT/US2015/037258.
International Search Report and Written Opinion dated May 28, 2021 for International Application No. PCT/US2021/025319.

METHODS FOR TREATING GI TRACT DISORDERS

CROSS-REFERENCE TO RELATED APPLICATIONS

This application is a Continuation of U.S. application Ser. No. 16/216,257, filed Dec. 11, 2018, which is a Continuation of U.S. application Ser. No. 15/717,765, filed Sep. 27, 2017, now abandoned, which is a Continuation of U.S. application Ser. No. 14/820,885, filed Aug. 7, 2015, now U.S. Pat. No. 9,808,467, which is a Continuation of U.S. application Ser. No. 14/555,455, filed Nov. 26, 2014, now U.S. Pat. No. 9,132,134, which is a continuation of International Patent Application No. PCT/US2013/076733, filed Dec. 19, 2013, which claims benefit of U.S. Provisional Patent Application No. 61/745,734, filed Dec. 24, 2012, each of which is incorporated herein by reference in its entirety. International Application PCT/US2013/076733 was published under PCT Article 21(2) in English.

BACKGROUND OF THE INVENTION

The enteric nervous system (ENS) comprises about one hundred million neurons embedded in the lining of the gastrointestinal system. The ENS innervates the gastrointestinal system, including the esophagus, the stomach (e.g., gastric area), and the intestines. Motor neurons of the ENS control stomach muscle contractility, peristalsis, and churning of intestinal contents. It has been estimated that about 50% of the body's dopamine is found in the ENS.

Gastrointestinal (GI) tract disorders affect many people. Irritable bowel syndrome (IBS), a disorder in which the intestine functions abnormally due to dysfunction of the muscles or nerves of the GI tract, affects 10 to 15% of the adult population. Symptoms of IBS include constipation, diarrhea, and abdominal pain. Functional dyspepsia (dyspepsia caused by a dysfunction of the muscles or nerves associated with the upper GI tract) affects 10 to 20% of the adult population. Gastroparesis, a disorder causing inadequate grinding of food by the stomach and delayed gastric emptying, affects up to 10% of the general population. Gastroesophageal reflux disorder (GERD), a chronic digestive disease that occurs when stomach acid and/or bile backs up into the esophagus, has been estimated to affect up to 35% of infants in the first few months of life.

In addition, gastrointestinal disorders can be associated with a number of other diseases. For example, some of the earliest symptoms of Parkinson's disease, a disorder characterized by neurodegeneration of dopamine neurons, include, e.g., constipation and other gastrointestinal symptoms, likely due to degeneration or dysfunction of ENS dopamine neurons. For other example, diabetes is one of the most common causes of gastroparesis, as chronic high blood sugar can damage the vagus nerve which modulates the enteric nervous system. Multiple sclerosis is another disease that is associated with ENS disorders such as, e.g., gastroparesis. Migraine headaches are commonly associated with gastric stasis. Chemotherapy-induced nausea and/or vomiting have been estimated to affect 85% of cancer patients undergoing chemotherapy and can result in discontinuation of treatment. If the chemotherapy-induced nausea and/or vomiting are not properly managed, it can cause dehydration and poor quality of life and may result in discontinuation of chemotherapy.

ENS dysfunction has been implicated in several of the disorders described above. For example, impaired or dysfunctional ENS neuronal signaling has been strongly implicated as a causative factor for gastroparesis.

There are currently no adequate treatments for these disorders. For example, IBS treatments lubiprostone and linaclotide are used to mimic infectious diarrhea in order to treat constipation; however, these agents do not correct the underlying ENS dysfunction and are marginally effective. The dopamine D2 receptor antagonists domperidone and metoclopramide have been previously indicated for the treatment of nausea and vomiting, however, their use is discouraged due to significant safety issues. Two significant safety concerns relate to (1) unwanted cardiac side effects caused by, e.g., interaction of the agents with ion channels involved in cardiac action potentials, and (2) unwanted motor dysfunction caused by the actions of the dopamine antagonists which cross the blood brain barrier into the brain. For example, it has been established that many dopamine receptor antagonists inhibit hERG channels (a type of potassium channel) to cause drug-induced long QT syndrome, a heart condition characterized by abnormal cardiac action potential rhythms. Long QT syndrome can increase risk of cardiac arrhythmias, which may lead to sudden cardiac death. Indeed, the dopamine D2 antagonist domperidone has been shown to inhibit hERG activity and increase risk of long QT syndrome, and increase risk of sudden cardiac death. This has resulted in an FDA ban on the use of domperidone in the United States and an initiated review of the safety of domperidone use by the European Medicines Agency. Metoclopramide cannot be taken for more than 12 weeks and has a black box warning for CNS-related side effects such as tardive dyskinesia, a difficult-to-treat and often incurable disorder characterized by involuntary, repetitive body movements.

SUMMARY OF THE INVENTION

Aspects of the present invention relate to methods of treating disorders, e.g., functional and motility disorders of the gastrointestinal (GI) tract. Such methods may comprise, e.g., modulating the enteric nervous system (ENS). For example, the present invention provides for a method of treating functional and motility disorders of the GI tract by administrating an effective amount of a peripherally-restricted dopamine receptor D2 antagonist that does not have adverse cardiac effects on an individual and modulating the enteric nervous system (ENS).

The present invention also provides for a method of treating gastroparesis by administering an effective amount of a composition of metopimazine, metopimazine acid, or a prodrug thereof, modulating the ENS, and treating gastroparesis.

The present invention also provides for a method of treating vomiting and nausea associated with a GI tract disorder, by administering an effective amount of a peripherally-restricted dopamine receptor D2 antagonist that does not have adverse cardiac effects on an individual, and modulating the ENS.

The present invention provides for a method of improving gastric emptying, by administering an effective amount of a peripherally-restricted dopamine receptor D2 antagonist that does not have adverse cardiac effects on an individual, and modulating the ENS.

The present invention further provides for a method of improving gastric emptying, by administering an effective amount of carbidopa, and modulating the ENS.

The present invention provides a method of treating functional and motility disorders of the GI tract, including the steps of: administrating an effective amount of a compound which is a peripherally-restricted dopamine receptor D2 antagonist that does not have adverse cardiac effects on an individual; and modulating the enteric nervous system (ENS). In some embodiments, the GI tract disorder is chosen from the group consisting of IBS/abdominal pain, functional dyspepsia, gastroparesis, cyclic vomiting syndrome, chemotherapy-induced nausea and vomiting. The invention also provides a method of treating gastroparesis, including the steps of: administering an effective amount of a compound chosen from the group consisting of metopimazine, metopimazine acid, and a prodrug thereof; modulating the enteric nervous system (ENS); and treating gastroparesis.

The invention also provides a method of treating vomiting and nausea associated with a GI tract disorder, including the steps of: administering an effective amount of a peripherally-restricted dopamine receptor D2 antagonist that does not have adverse cardiac effects on an individual; and modulating the enteric nervous system (ENS).

The invention also provides a method of improving gastric emptying, including the steps of: administering an effective amount of a peripherally-restricted dopamine receptor D2 antagonist that does not have adverse cardiac effects on an individual; and modulating the enteric nervous system (ENS).

In any of the foregoing methods, the compound may be chosen from the group consisting of metopimazine and metopimazine acid, and prodrugs thereof. In some embodiments, the compound is a prodrug of metopimazine acid chosen from the group consisting of ethyl 1-[3-(2-methylsulfonylphenothiazin-10-yl)propyl]piperidine-4-carboxylate, [2-(dimethylamino)-2-oxo-ethyl] 1-[3-(2-methylsulfonylphenothiazin-10-yl)propyl]piperidine-4-carboxylate, 2-dimethylaminoethyl 1-[3-(2-methylsulfonylphenothiazin-10-yl)propyl]piperidine-4-carboxylate, 1-(2-methylpropanoyloxy)ethyl 1-[3-(2-methylsulfonylphenothiazin-10-yl)propyl]piperidine-4-carboxylate, and 2-[[1-[3-(2-methylsulfonylphenothiazin-10-yl)propyl]piperidine-4-carbonyl]amino]propanoic acid. In some embodiments, the composition is administered at 10 mg to 60 mg every four hours.

The invention also provides a method of improving gastric emptying, including the steps of: administering an effective amount of carbidopa; and modulating the enteric nervous system (ENS). In some embodiments, the method further includes the step of administering an effective amount of the peripherally-restricted dopamine receptor D2 antagonist that does not have adverse cardiac effects on an individual chosen from the group consisting of metopimazine, metopimazine-acid (MPZA), and prodrugs thereof.

The invention also provides a method of treating an enteric nervous system disorder in a human subject in need thereof, comprising administering to the subject an effective dose of a compound comprising a phenothiazine group or a pharmaceutically acceptable salt, solvate, metabolite, or prodrug thereof to the subject for over 5 days.

The invention also provides a method of treating an enteric nervous system disorder in a subject in need thereof, comprising administering to the subject an effective dose of a compound comprising a phenothiazine group or a pharmaceutically acceptable salt, solvate, metabolite, or prodrug thereof to the subject for over 7 days.

The invention also provides a method of treating an enteric nervous system disorder in a subject in need thereof, comprising co-administering to the subject an effective dose of compound comprising a phenothiazine group or a pharmaceutically acceptable salt, solvate, metabolite, or prodrug thereof, and a dopamine decarboxylase inhibitor.

The invention also provides a method of treating an enteric nervous system disorder in a subject in need thereof, comprising administering to the subject an effective dose of a dopamine decarboxylase inhibitor. In some embodiments, the dopamine decarboxylase inhibitor does not cross a blood-brain barrier of the subject. In some embodiments, the dopamine decarboxylase inhibitor is carbidopa. In some embodiments, the dopamine decarboxylase inhibitor is selected from the group consisting of Benserazide, Methyldopa, or α-Difluoromethyl-DOPA (DFMD, DFM-DOPA).

The invention also provides a method of treating an enteric nervous system disorder in a human subject in need thereof, comprising administering to the subject a compound that is a peripherally restricted dopamine D2 receptor antagonist, or a pharmaceutically acceptable salt, solvate, metabolite, or prodrug thereof, for over 12 weeks, wherein the peripherally restricted dopamine D2 receptor antagonist is not domperidone and is not a compound of Formula (Y):

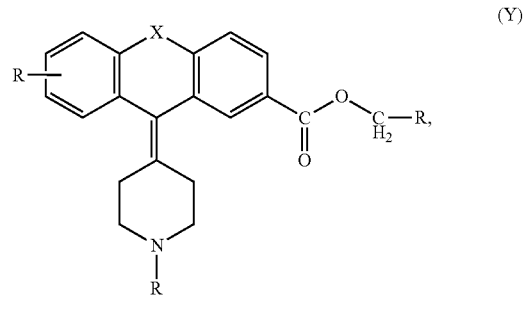

wherein X is —CH═CH—, —CH$_2$—CH$_2$—, —CH$_2$—O—, —O—CH$_2$—, —S—CH$_2$—, CH$_2$—S—, —S—, or —O—, and R is a 5- or 6-membered nitrogen heterocyclic ring optionally fused to a benzo group. In some embodiments, the peripherally restricted dopamine D2 receptor antagonist exhibits minimal hERG inhibition.

In any of the foregoing methods, the compound may comprise the structure of Formula I

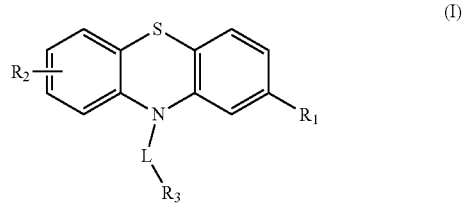

wherein, $R_1$ and $R_2$ are each independently selected from H, cyano, nitro, azido, halo, —CF$_3$, unsubstituted $C_1$-$C_4$ alkyl, —SR$_4$, —S(O)R$_4$, —S(O)$_2$R$_4$, —NR$_4$R$_4$, —OR$_4$ and $C_1$-$C_4$ alkyl substituted with halo, —OR$_4$, —SR$_4$, —S(O)R$_4$, —S(O)$_2$R$_4$, and —OR$_4$; each $R_4$ is independently selected from H and $C_1$-$C_4$ alkyl; L a bond or $C_1$-$C_{10}$ alkyl optionally substituted with —OR$_4$ or —NR$_4$R$_4$; and $R_3$ is H, —NR$_4$R$_4$, or $C_3$-$C_7$ heterocycloalkyl having 1, 2, or 3 heteroatoms selected from N, O, and S in the ring, wherein the heterocycloalkyl group if present is optionally substituted with an aryl group, R$_4$, —CO$_2$H, —CO$_2$R$_4$, —C(O)NR$_4$R$_4$ and or $C_1$-$C_4$ alkyl optionally substituted with —OR$_4$, —NR$_4$R$_4$.

In some embodiments, the compound has the structure of the Formula II

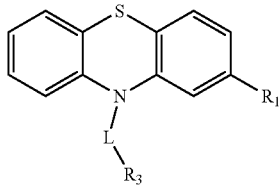
(II)

wherein: $R_1$ is H, halo, —$CF_3$, unsubstituted $C_1$-$C_4$ alkyl, —$SR_4$, —$S(O)R_4$, —$S(O)_2R_4$, or —$OR_4$; each $R_4$ is independently selected from H and $C_1$-$C_4$ alkyl; L is a bond or $C_1$-$C_6$ alkyl; and $R_3$ is H, —$NR_4R_4$, or $C_3$-$C_7$ heterocycloalkyl having 1, 2, or 3 heteroatoms selected from N, O, and S in the ring, wherein the heterocycloalkyl group if present is optionally substituted with, —$CO_2H$, —$CO_2R_4$, —$C(O)NR_4R_4$, and or $C_1$-$C_4$ alkyl optionally substituted with —$OR_4$, —$NR_4R_4$.

In some embodiments, the compound is a compound of Formula III

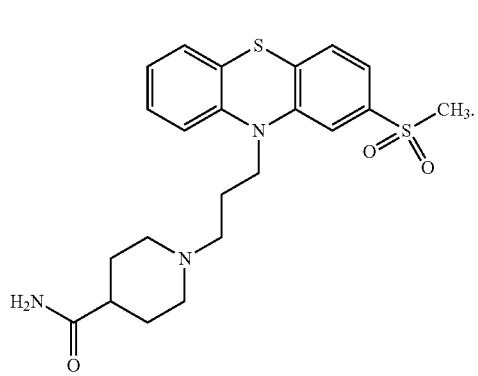
(III)

In some embodiments, the compound is of Formula IV:

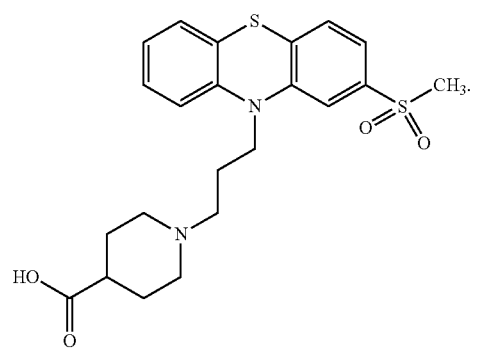
(IV)

In some embodiments, the compound is of Formula V:

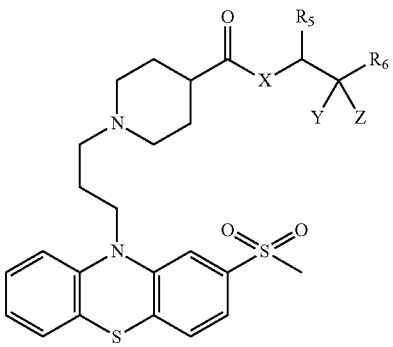
(V)

wherein X is O or NH; $R_5$ is $C_1$-$C_6$ linear or branched alkyl, benzyl, $CH_2OH$, $CH_2CH_2OH$, or $CH_2CH_2SMe$; Y and Z are both hydrogen or together can be a carbonyl oxygen; $R_6$ is OH, $OR_7$, or $NR_8R_9$; and $R_7$, $R_8$, and $R_9$ are independently $C_1$-$C_4$ linear or branched alkyl.

In some embodiments, the compound is of Formula VI:

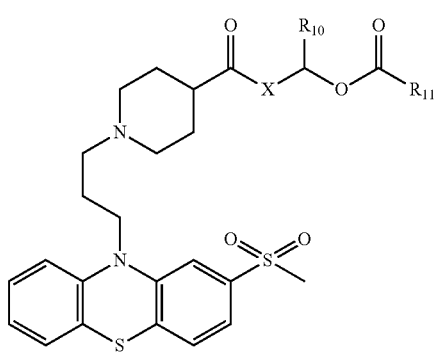
(VI)

wherein $R_{10}$ is $C_1$-$C_4$ linear or branched alkyl; and $R_{11}$ is $C_1$-$C_6$ linear or branched alkyl, phenyl, or $C_4$-$C_7$ cycloalkyl.

In some embodiments, the compound is of Formula VII:

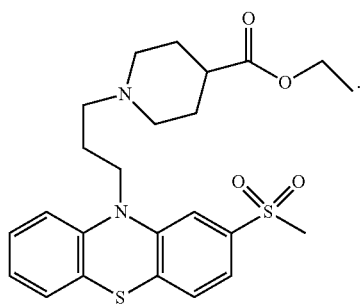
(VII)

In some embodiments, the compound is of Formula VIII:

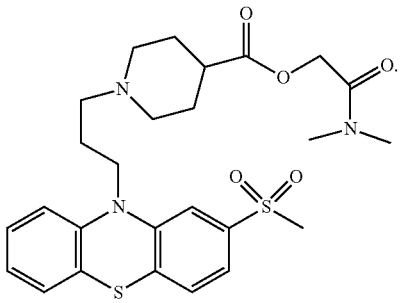

(VIII)

In some embodiments, the compound is of Formula IX:

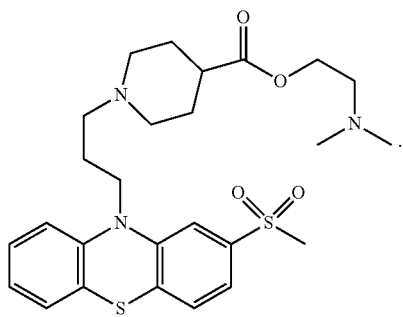

(IX)

In some embodiments, the compound is of Formula X:

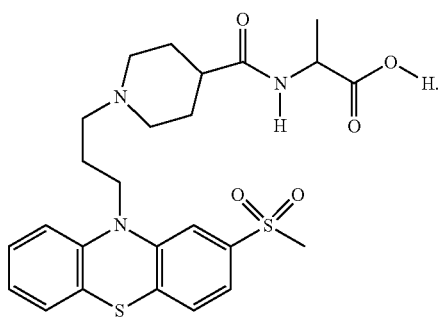

(X)

In some embodiments, the compound is of Formula XI:

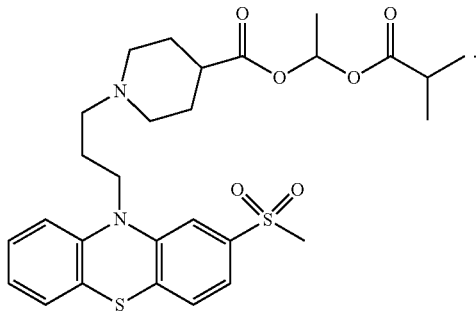

(XI)

In some embodiments of methods described herein, the subject is a mammal. In some embodiments, the mammal is a human. In some embodiments, the subject is not an adult. In some embodiments, the enteric nervous system disorder is a chronic disorder. In some embodiments, the enteric nervous system disorder is selected from the group consisting of gastroparesis, Irritable Bowel Syndrome, lysosomal storage disorders, intestinal dysmotility, ganglioneuroma, multiple endocrine neoplasia type 2B (MEN2B), gastrointestinal neuropathy, and intestinal neuronal dysplasia. In some embodiments, the enteric nervous system disorder is gastroparesis. In some embodiments, the disorder has a symptom which is selected from the group consisting of nausea, vomiting, delayed gastric emptying, diarrhea, abdominal pain, gas, bloating, gastroesophageal reflux, reduced appetite, and constipation. In some embodiments, the symptom is associated with Scleroderma, Parkinson's Disease, gastroesophageal reflux disease, Menetrier's Disease, a vestibular disorder, chemotherapy, cancer, drug use, and functional dyspepsia.

In any of the foregoing methods, the compound may be administered orally, parenterally, enterally, intraperitoneally, topically, transdermally, ophthalmically, intranasally, locally, non-orally, via spray, subcutaneously, intravenously, intratonsillary, intramuscularly, buccally, sublingually, rectally, intra-arterially, by infusion, or intrathecally. In any of the foregoing methods, the compound may be formulated in a pharmaceutical composition comprising a physiologically acceptable vehicle. In some embodiments, the pharmaceutical composition is formulated as a tablet, a capsule, a cream, a lotion, an oil, an ointment, a gel, a paste, a powder, a suspension, a syrup, an enema, an emulsion, or a solution, a controlled-release formulation. In some embodiments, the pharmaceutical composition is a syrup, an enema, or a tablet. In some embodiments, the tablet is an orally disintegrating tablet. In some embodiments, the method comprises administering more than 30 mg of the compound a day. In some embodiments, the method comprises administering the compound for over 12 weeks. In some embodiments, the method comprises administering the compound four times per day.

In some embodiments of any of the foregoing methods, the administering does not increase probability that the subject will suffer an adverse cardiac side effect. In some embodiments, the administering does not increase probability that the subject will suffer an adverse extrapyramidal side effect in the subject. In some embodiments, the compound does not effectively cross a blood brain barrier. For example, in some embodiments, the dopamine decarboxylase inhibitor does not cross a blood brain barrier. In some embodiments, the dopamine decarboxylase inhibitor is carbidopa.

In some embodiments of any of the foregoing methods, the method comprises coadministering an additional therapeutic agent. In some embodiments, the additional therapeutic agent is selected from the group consisting of serotonin agonists, serotonin antagonists, selective serotonin reuptake inhibitors, anticonvulsants, opioid receptor agonists, bradykinin receptor antagonists, NK receptor antagonists, adrenergic receptor agonists, benzodiazepines, gonadotropin-releasing hormone analogues, calcium channel blockers, and somatostatin analogs. In some embodiments, the coadministering comprises administering the additional therapeutic agent in a single composition with the compound and/or dopamine decarboxylase inhibitor. In some embodiments, the coadministering comprises administering the additional therapeutic agent sequentially with the compound and/or dopamine decarboxylase inhibitor. In some embodiments, the coadministering comprises administering the additional therapeutic agent simultaneously with the compound and/or dopamine decarboxylase inhibitor.

The invention also provides a kit, comprising: (a) at least one unit dosage of a pharmaceutical composition comprising a compound of Formula I:

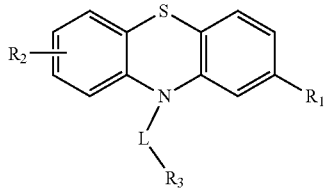

wherein, $R_1$ and $R_2$ are each independently selected from H, cyano, nitro, azido, halo, —$CF_3$, unsubstituted $C_1$-$C_4$ alkyl, —$SR_4$, —$S(O)R_4$, —$S(O)_2R_4$, —$NR_4R_4$, —$OR_4$ and $C_1$-$C_4$ alkyl substituted with halo, —$OR_4$, —$SR_4$, —$S(O)R_4$, —$S(O)_2R_4$, and —$OR_4$; each $R_4$ is independently selected from H and $C_1$-$C_4$ alkyl; L a bond or $C_1$-$C_{10}$ alkyl optionally substituted with —$OR_4$ or —$NR_4R_4$; and $R_3$ is H, —$NR_4R_4$, or $C_3$-$C_7$ heterocycloalkyl having 1, 2, or 3 heteroatoms selected from N, O, and S in the ring, wherein the heterocycloalkyl group if present is optionally substituted with an aryl group, $R_4$, —$CO_2H$, —$CO_2R_4$, —$C(O)NR_4R_4$ and or $C_1$-$C_4$ alkyl optionally substituted with —$OR_4$, —$NR_4R_4$; and (b) instructions for carrying out any of the foregoing methods. In some embodiments, the compound has the structure of the Formula II:

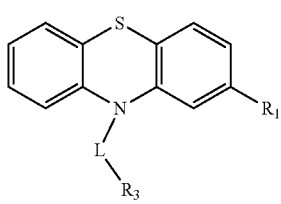

wherein: $R_1$ is H, halo, —$CF_3$, unsubstituted $C_1$-$C_4$ alkyl, —$SR_4$, —$S(O)R_4$, —$S(O)_2R_4$, or —$OR_4$; each $R_4$ is independently selected from H and $C_1$-$C_4$ alkyl; L is a bond or $C_1$-$C_6$ alkyl; and $R_3$ is H, —$NR_4R_4$, or $C_3$-$C_7$ heterocycloalkyl having 1, 2, or 3 heteroatoms selected from N, O, and S in the ring, wherein the heterocycloalkyl group if present is optionally substituted with, —$CO_2H$, —$CO_2R_4$, —$C(O)NR_4R_4$, and or $C_1$-$C_4$ alkyl optionally substituted with —$OR_4$, —$NR_4R_4$.

In some embodiments, the compound is a compound of Formula III:

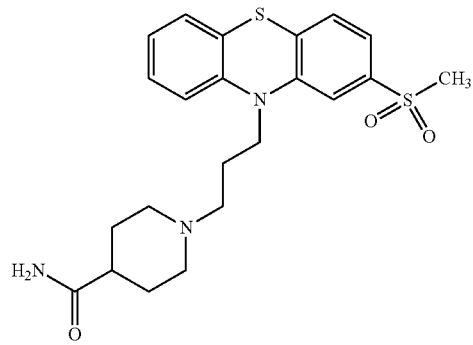

In some embodiments, the compound is of Formula IV:

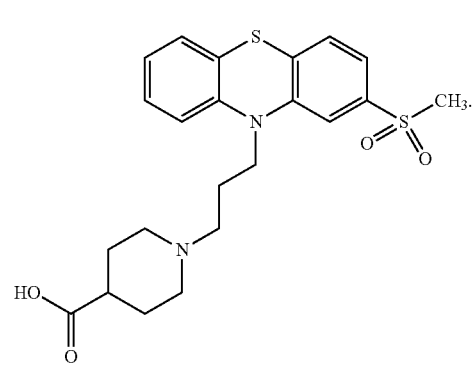

In some embodiments, the compound is of Formula V:

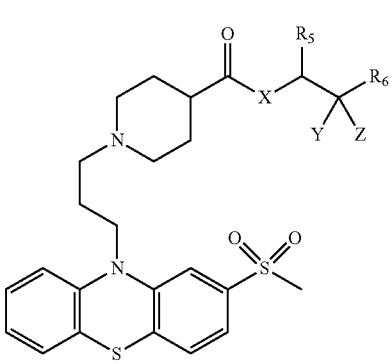

wherein X is O or NH; $R_5$ is $C_1$-$C_6$ linear or branched alkyl, benzyl, $CH_2OH$, $CH_2CH_2OH$, or $CH_2CH_2SMe$; Y and Z are both hydrogen or together can be a carbonyl oxygen; $R_6$ is OH, $OR_7$, or $NR_8R_9$; and $R_7$, $R_8$, and $R_9$ are independently $C_1$-$C_4$ linear or branched alkyl.

In some embodiments, the compound is of Formula VI:

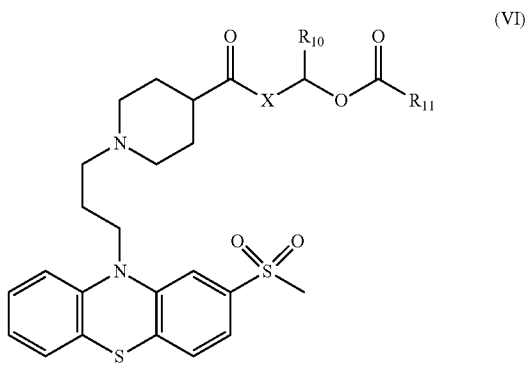

(VI)

wherein $R_{10}$ is $C_1$-$C_4$ linear or branched alkyl; and $R_{11}$ is $C_1$-$C_6$ linear or branched alkyl, phenyl, or $C_4$-$C_7$ cycloalkyl.

In some embodiments, the compound is of Formula VII:

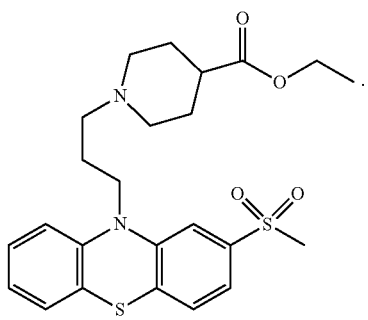

(VII)

In some embodiments, the compound is of Formula VIII:

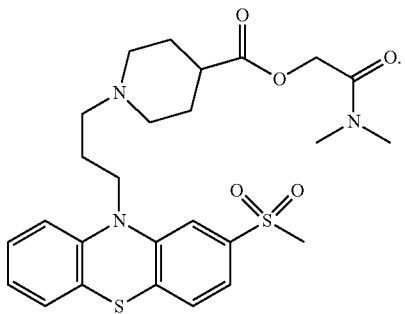

(VIII)

In some embodiments, the compound is of Formula IX:

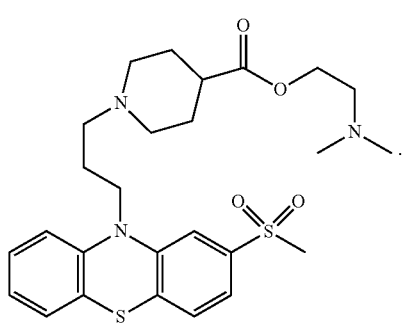

(IX)

In some embodiments, the compound is of Formula X:

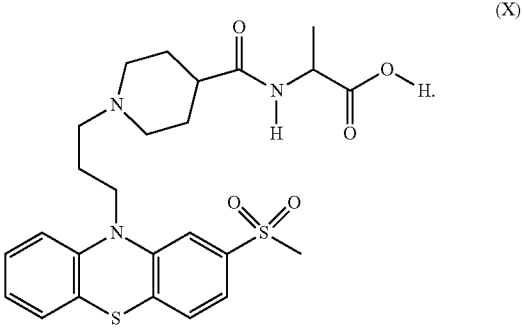

(X)

In some embodiments, the compound is of Formula XI:

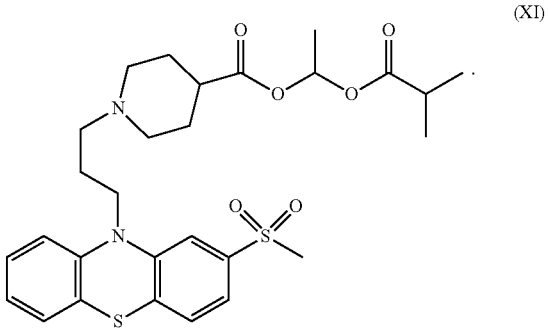 [SMILES: CC(OC(=O)C(C)C)OC(=O)C1CCN(CCCN2c3ccccc3Sc3ccc(S(C)(=O)=O)cc32)CC1]

(XI)

The invention also provides a kit, comprising: (a) at least one unit dosage of a pharmaceutical composition comprising a dopamine decarboxylase inhibitor; and (b) instructions for carrying out any of the foregoing methods. In some embodiments, the dopamine decarboxylase inhibitor does not cross a blood-brain barrier of the subject. In some embodiments, the dopamine decarboxylase inhibitor is carbidopa. In some embodiments, the dopamine decarboxylase inhibitor is selected from the group consisting of Benserazide, Methyldopa, or α-Difluoromethyl-DOPA (DFMD, DFM-DOPA). In some embodiments, the kit further comprises at least one dosage form of a composition comprising a compound of any one of Formulas I-XI described herein.

In some embodiments, the invention provides a use of any of the foregoing compounds in the preparation of a medicament for the treatment of a disorder, e.g., an enteric nervous system disorder. In some embodiments, the medicament is prepared for administration for over 5 days.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
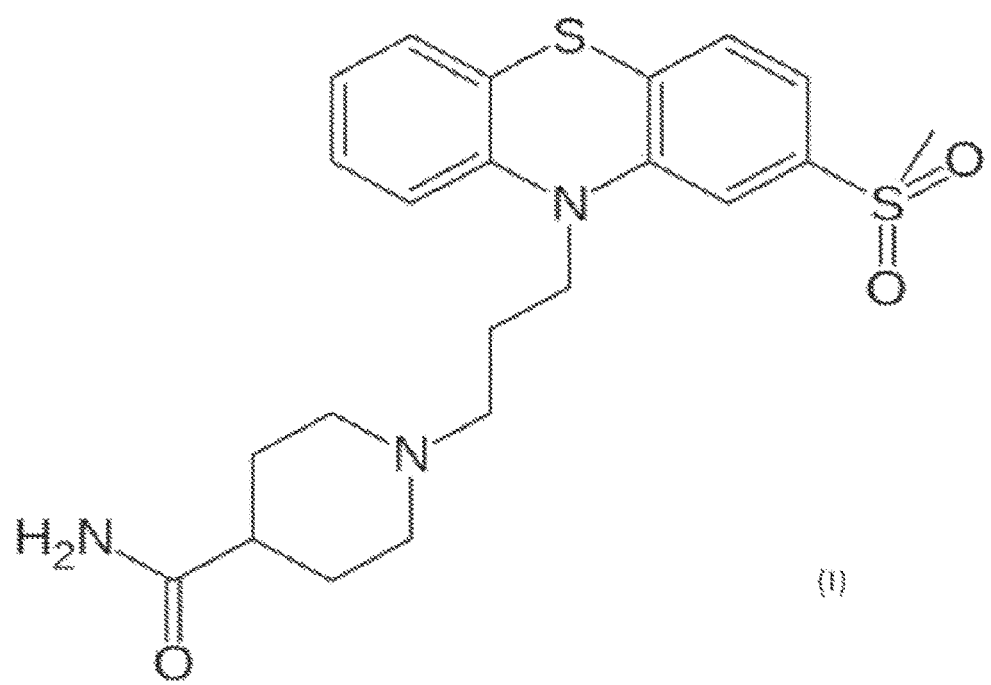
FIG. 1 depicts a drawing of the chemical structure of metopimazine.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Sambrook, Fritsch and Maniatis, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), and CULTURE OF ANIMAL CELLS: A MANUAL OF BASIC TECHNIQUE AND SPECIALIZED APPLICATIONS, 6th Edition (R. I. Freshney, ed. (2010), which are hereby incorporated by reference.

As used in the specification and claims, the singular forms "a", "an" and "the" include plural references unless the context clearly dictates otherwise. For example, the term "a cell" includes a plurality of cells, including mixtures thereof.

Definitions

The term "agonist," as used herein, generally refers to a molecule such as a compound, a drug, an enzyme activator or a hormone modulator that binds to a specific receptor and triggers a response in the cell. An agonist generally mimics the action of an endogenous ligand (such a, e.g., dopamine) that binds to the same receptor.

The term "antagonist," as used herein, refers to a molecule such as a compound, which diminishes, inhibits, or prevents a cellular response to a receptor activated by an agonist. Antagonists can include, but are not limited to, competitive antagonists, non-competitive antagonists, uncompetitive antagonists, partial agonists and inverse agonists. Competitive antagonists can reversibly bind to receptors at the same binding site (active site) as the endogenous ligand or agonist, without necessarily activating the receptor. Non-competitive antagonists (also known as allosteric antagonists) can bind to a distinctly separate binding site from the agonist, exerting their action to that receptor via the other binding site. Non-competitive antagonists generally do not compete with agonists for binding. Binding of a non-competitive antagonist to the receptor may result in a decreased affinity of an agonist to that receptor. Alternatively, binding of a non-competitive antagonist to a receptor may prevent a conformational change in the receptor required for agonist-mediated receptor activation. Uncompetitive antagonists may require receptor activation by an agonist before they can bind to a separate allosteric binding site. Partial agonists can refer to molecules which, at a given receptor, might differ in the amplitude of the functional response they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone. An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but inhibit the basal activity of the receptor.

As used herein, a compound that is "peripherally restricted" generally refers to a compound that does not substantially cross an intact blood brain barrier of a subject. The term also encompasses compounds that may cross an intact blood brain barrier, but upon administration to a subject is rapidly metabolized to a form that does not substantially cross an intact blood brain barrier of the subject. A compound may be considered "peripherally restricted" if, upon administration to a subject, less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.1% of the compound crosses an intact blood brain barrier of the subject.

As used herein, the terms "treatment" or "treating" are used interchangeably herein. These terms refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. For prophylactic benefit, the compositions may be administered to a subject at risk of developing a particular disease, or to a subject reporting one or more of the physiological symptoms of a disease, even though a diagnosis of this disease may not have been made.

A "sub-therapeutic amount" of an agent is an amount less than the effective amount for that agent. When combined with an effective or sub-therapeutic amount of one or more additional agents, the sub-therapeutic amount can produce a result desired by the physician, due to, for example, synergy in the resulting efficacious effects, or reduced adverse effects.

A "synergistically effective" therapeutic amount or "synergistically effective" amount of an agent or therapy is an amount which, when combined with an effective or sub-therapeutic amount of one or more additional agents, produces a greater effect than when either of the agents are used alone. In some embodiments, a synergistically effective therapeutic amount of an agent or therapy produces a greater effect when used in combination than the additive effects of any of the individual agents when used alone. The term "greater effect" encompasses not only a reduction in symptoms of the disorder to be treated, but also an improved side effect profile, improved tolerability, improved patient compliance, improved efficacy, or any other improved clinical outcome.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "prodrug", as used herein, generally refers to an agent that is converted into the parent drug in vivo.

The term "alkyl", as used herein, refers to a hydrocarbon chain that is a straight chain or branched chain, containing the indicated number of carbon atoms. For example, $C_1$-$C_4$ alkyl group indicates that the group has from 1 to 4 (inclusive) carbon atoms in it. Similarly, $C_1$-$C_{10}$ alkyl group indicates that the group has from 1 to 10 (inclusive) carbon atoms in it. The alkyl may be unsubstituted or substituted with one or more substituents.

The term "halo" or "halogen", as used herein, refers to fluoro, chloro, bromo, or iodo.

The term "cycloalkyl", as used herein, refers to a carbon cyclic aliphatic ring structure, for example, a 4-7 carbon cyclic structure. The cycloalkyl may be unsubstituted or substituted with one or more substituents.

The term "heterocycloalkyl" or "heterocyclic ring" refers to a substituted or unsubstituted 3-, 4-, 5-, 6- or 7-membered saturated or partially unsaturated ring containing one, two, or three heteroatoms, independently selected from oxygen, nitrogen and sulfur; Heterocycloalkyl may be unsubstituted or substituted with one or more substituents. The heterocycloalkyl may be optionally fused to another cycloalkyl, heterocycloalkyl, or an aryl. For example, to a benzo group.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., benzyl, phenyl, fluorenyl, and naphthyl). The term includes monocyclic or fused-ring polycyclic groups. An aryl moiety is unsubstituted or substituted with one or more substituents.

The term "cyano", as used herein, refers to a carbon linked to a nitrogen by a triple bond, i.e., —C≡N.

The term "nitro", as used herein, refers to a $NO_2$ substituent.

The term "azido", as used herein refers to a $N_3$ substituent.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof Overview Certain phenothiazine compounds can be safely administered to a subject without increasing risk of an adverse cardiac symptom or increasing risk of an adverse motor symptom in the subject. Accordingly, the invention provides a method, comprising administering to a subject a compound comprising a phenothiazine group or a pharmaceutically acceptable salt, solvate, metabolite, or prodrug thereof to the subject for over 5 days. In some embodiments, the administering effectively treats a disorder in the subject. The disorder can be, e.g., a gastrointestinal disorder, and/or an ENS disorder. The invention also provides a method of treating an ENS disorder in a subject in need thereof, comprising administering to the subject a compound that is a peripherally restricted dopamine D2 receptor antagonist, or a pharmaceutically acceptable salt, solvate, metabolite, or prodrug thereof, for over 12 weeks. In some embodiments, the peripherally restricted dopamine D2 receptor antagonist is not domperidone and is not a compound of Formula (Y):

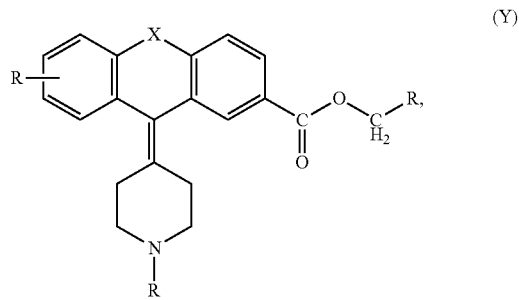

wherein X is —CH=CH—, —CH$_2$—CH$_2$—, —CH$_2$—O—, —O—CH$_2$—, —S—CH$_2$—S—, —S—, or —O—, and R is a 5- or 6-membered nitrogen heterocyclic ring optionally fused to a benzo group.

Some dopamine decarboxylase inhibitors can effectively promote gastric motility.

Accordingly, the invention provides a method of treating an ENS disorder in a subject in need thereof, comprising administering to the subject an effective dose of a dopamine decarboxylase inhibitor. In some embodiments, the method comprises co-administering to the subject an effective dose of compound comprising a phenothiazine group or a pharmaceutically acceptable salt, solvate, metabolite, or prodrug thereof, and a dopamine decarboxylase inhibitor.

Exemplary Subjects

The compounds can be used for the treatment of a disorder in a subject in need thereof. The subject may be suffering from, may be diagnosed with, may be exhibiting a symptom of, or may be suspected of having the disorder. The disorder can be a gastrointestinal disorder, an enteric nervous system disorder, or other disorder. The disorder may be characterized by a hypomotility of at least a portion of the gastrointestinal tract. For example, the disorder can be characterized by hypomotility of the stomach and/or intestine. The hypomotility may be caused by aberrant ENS neuronal signaling, for example, by aberrant dopamine signaling activity.

In some embodiments, the enteric nervous system disorder is gastroparesis. The terms "gastroparesis" and "delayed gastric emptying" are used interchangeably herein to refer to a disorder that, e.g., slows or stops the movement of food from the stomach to the small intestine. Normally, the muscles of the stomach, which are controlled by the vagus nerve, contract to break up food and move it through the gastrointestinal (GI) tract. Gastroparesis can occur, for example, when the vagus nerve is damaged by illness or injury, causing the stomach muscles stop working normally. In subjects with gastroparesis, food can move slowly from the stomach to the small intestine or may stop moving altogether. Accordingly, the subject may be suffering from, may be diagnosed with, may be exhibiting a symptom of, or may be suspected of having gastroparesis.

A subject may be suspected of having gastroparesis if the subject exhibits or has exhibited a symptom of gastroparesis. Symptoms of gastroparesis can include gastroesophageal reflux (GER), also called acid reflux or acid regurgitation. Gastroesophageal reflux generally refers to a condition in which stomach contents flow back up into the esophagus. Other symptoms associated with gastroparesis include, but are not limited to, pain and/or burning sensation in the stomach area, abdominal bloating, lack of appetite, anorexia, malnutrition, nausea, and vomiting. A symptom of gastroparesis can be mild or severe, and can occur frequently or infrequently. A symptom of gastroparesis can vary in severity over time in the same subject. Accordingly, the subject may exhibit or has exhibited GER, pain and/or burning sensation in the stomach area, abdominal bloating, lack of appetite, anorexia, malnutrition, nausea, and/or vomiting.

The subject may be diagnosed with gastroparesis. Gastroparesis may be diagnosed by any means known to those of skill in the art or otherwise described herein. Gastroparesis may be diagnosed, e.g., through a physical exam, medical history, blood tests, tests to rule out blockage or structural problems in the GI tract, gastric emptying assays, and assays of GI contractile activity. Tests may also identify a nutritional disorder or underlying disease. Tests that are useful in diagnosing gastroparesis include, but are not limited to, upper gastrointestinal (GI) endoscopy, upper GI series, ultrasound tests, gastric emptying scintigraphy, gastric emptying breath test, antral manometry, electrogastrography, and/or electrogastroenterography.

Upper GI endoscopy can be used to rule out other conditions that could result in delayed gastric emptying (such as, e.g., a physical obstruction). Upper GI endoscopy typically involves use of an endoscope (e.g., a small, flexible tube with a light) to visualize the upper GI tract, including, e.g., the esophagus, stomach, and duodenum (the first part of the small intestine). The endoscope is generally used to image the stomach and/or duodenum. A small camera mounted on the endoscope can transmit a video image to a monitor, allowing close examination of the intestinal lining. Upper GI endoscopy may show physical blockage of the upper GI tract, for example, a large bezoar (e.g., solid collections of food, mucus, vegetable fiber, hair, or other material). In some embodiments, the subject is diagnosed with gastroparesis if the subject exhibits a symptom of gastroparesis and upper GI endoscopy does not reveal a physical blockage causing the delayed gastric emptying.

An upper GI series may be performed to look at the small intestine. The test may be performed at a hospital or outpatient center by an x-ray technician, and the images may be interpreted by a radiologist. During the procedure, the subject may stand or sit in front of an x-ray machine and drink barium, a chalky liquid. Barium may coat the small intestine, making signs of gastroparesis show up more clearly on x rays. Gastroparesis may be indicated in cases wherein the x-ray shows food in the stomach after fasting. In some embodiments, the subject is diagnosed with gastroparesis if an upper GI series reveals food in the stomach after fasting.

Ultrasound can be useful in ruling out other syndromes which may share symptoms in common with gastroparesis. Such other syndromes include gallbladder disease and pancreatitis. Ultrasound generally uses a device, called a transducer, that bounces safe, painless sound waves off organs to create an image of their structure. The procedure can be performed in a health care provider's office, outpatient center, or hospital by a specially trained technician. Ultrasound images may be interpreted by a radiologist. The subject may be diagnosed with gastroparesis if the subject exhibits a symptom of gastroparesis and other syndromes such as, e.g., gallbladder disease, pancreatitis, are ruled out by, for example, ultrasound.

Gastric emptying scintigraphy can be used to diagnose gastroparesis in a subject. Gastric emptying scintigraphy can involve ingestion of a bland meal—such as eggs or an egg substitute—that contains a small amount of radioactive material. The radioactive material may be 99-M Technetium (TC) sulfur colloid or other radioactive ligand. The test may be performed in a radiology center or hospital. An external camera may be used to detect and/or measure radioactivity in the abdominal region. Radioactivity may be measured at timed intervals, e.g., at 1, 2, 3, and 4 hours after the meal. Gastroparesis may be positively identified in subjects exhibiting more than 10 percent of the meal within the stomach at 4 hours. Other measures of gastric emptying include, but are not limited to, the time at which 50% of the meal has been emptied out of the stomach. See, e.g., Thomforde, G. M. et al., Evaluation of an inexpensive screening scintigraphic test of gastric emptying, 36 J. Nucl. Med. 93 (1995), hereby incorporated by reference. In some embodiments, the subject is diagnosed with gastroparesis via gastric emptying scintigraphy.

A breath test useful for assessing gastric emptying can utilize radioactively labeled food (e.g., labeled with $C^{13}$-octanoic acid). $C^{13}$ from the food may be absorbed when it reaches the small bowel. The absorbed $C^{13}$ can then be rapidly metabolized in the liver to produce $^{13}CO_2$. The produced $^{13}CO_2$ may then be detected in the breath of the subject. The subject's breath may be collected and sampled at defined intervals. The samples may be analyzed for $^{13}CO_2$ by any means known in the art. The rate of appearance of $^{13}CO_2$ in the breath can be used to indicate the rate of gastric emptying. An exemplary method of performing a $C^{13}$-octanoic acid breath test is described in Ghoos, Y. S., et al., 104 Gastroenterology 1640-1647 (1993), hereby incorporated by reference. In some embodiments, the subject is diagnosed with gastroparesis via a breath test.

Manometry generally refers to the assessment of pressure changes in a lumen. Antral manometry, which can also be referred to as antro-duodenal manometry, generally refers to techniques for the evaluation of contractile activity in the distal stomach and duodenum. Intraluminal pressure of the stomach and/or duodenum can be measured through pressure sensors which are introduced into the lumen via a catheter. Measurements may be recorded over time in order to assess intraluminal pressure changes. Recordings may last for any amount of time. Intraluminal pressure changes can be used to indicate contractile patterns in the stomach and/or duodenum. Intraluminal pressure changes may be measured in a fasting state and/or after ingestion of a meal (post-prandially). Post-prandial contractile hypomotility can be indicative of gastroparesis in a subject. Accordingly, a subject may exhibit post-prandial gastric hypomotility, as determined by manometry.

Electrogastrography generally refers to techniques and methods for recording electrical activity of the stomach. Likewise, electrogastroenterography refers to techniques and methods for recording electrical activity of the stomach and small intestine. Such electrical activity can be recorded from the gastrointestinal mucosa, serosa, or the outer skin surface (cutaneously). Gastrointestinal mucosa can refer to the mucous membrane layer of the GI tract. Gastrointestinal serosa can comprise a thin layer of cells which secrete serous fluid, and a thin epithelial layer. Recordings can be made during a fasting state, and after ingestion of a meal (usually 60 minutes). Deviations from the normal frequency of electrical activity can include bradygastria and/or tachygastria. Control subjects typically exhibit an increase in electrical activity after a meal, indicative of increased GI motility. Subjects with aberrant GI motility can exhibit abnormal rhythms in activity and/or impairments in the postprandial increase. A normal frequency of GI electrical activity can be, e.g., 3 cycles per minute. Bradygastria, which can be characterized as a frequency of GI electrical activity that is decreased from normal, e.g., that is less than 2 cycles per minute for at least one minute, can be indicative of gastroparesis. In some embodiments, a subject may exhibit bradygastria. Electrogastrography (EGG) which measures electrical activity with cutaneous electrodes similar to those used in electrocardiograms can also be used to diagnose gastroparesis. (Stern, R. N. et al. EGG: Common issues in validation and methodology, 24 Psychophysiology 55-64 (1987)), hereby incorporated by reference. Accordingly, a subject may be diagnosed with gastroparesis as determined by electrogastrography.

The subject may be suffering from, may be diagnosed with, may be exhibiting a symptom of, or may be suspected of having gastroesophageal reflux disease (GERD). GERD can be a chronic condition resulting in gastroesophageal reflux. Symptoms of GERD include, e.g., heartburn, dry, chronic cough, wheezing, athsma, recurrent pneumonia, nausea, vomiting, sore throat, difficulty swallowing, pain in the chest or upper abdomen, dental erosion, bad breath, spitting up. GERD may be diagnosed with the aid of tests. Tests that are useful in the diagnosis of GERD include, e.g., upper GI series, described herein, upper endoscopy, esophageal pH monitoring, and esophageal manometry.

The subject may be suffering from, may be diagnosed with, may be exhibiting a symptom of, or may be suspected of having enteric nervous system disorder which is associated with a vestibular disorder of the ear. The vestibular disorder of the ear can be Menetrier's disease. Ménétrier disease can be characterized by enlargement of ridges (also referred to herein as rugae) along the inside of the stomach wall, forming giant folds in the lining of the stomach. Ménétrier disease may also cause a decrease in stomach acid resulting from a reduction in acid-producing parietal cells. Symptoms of Ménétrier disease include, by way of example only, severe stomach pain, nausea, frequent vomiting, and the like.

The subject may be suffering from, may be diagnosed with, may be exhibiting a symptom of, or may be suspected of having cyclical vomiting syndrome (CVS). Cyclical vomiting syndrome can be characterized by episodes or cycles of severe nausea and vomiting that alternate with symptom-free intervals. Such episodes can last for hours, or even days. Episodes can start at the same time of day, can last the same length of time, and can occur with the same symptoms and level of intensity. Episodes can be so severe that a person has to stay in bed for days, unable to go to school or work. Other symptoms of cyclical vomiting syndrome include, e.g., abdominal pain, diarrhea, fever, dizziness, and sensitivity to light during vomiting episodes. Continued vomiting may cause severe dehydration that can be life threatening. Symptoms of dehydration include thirst, decreased. Cyclical vomiting syndrome may be diagnosed in a subject who has experienced the following symptoms for at least 3 months: vomiting episodes that start with severe vomiting—several times per hour—and last less than 1 week, three or more separate episodes of vomiting in the past year, and absence of nausea or vomiting between episodes.

The subject may be suffering from, may be diagnosed with, may be exhibiting a symptom of, or may be suspected of having Irritable Bowel Syndrome (IBS). IBS generally refers to a syndrome in which subjects experience recurrent or chronic gastrointestinal symptoms. Symptoms of IBS can include, e.g., abdominal pain, abdominal discomfort, constipation, diarrhea, mucus in the stool, abdominal bloating, or a combination of any of the above. IBS may be diagnosed when a person has had abdominal pain or discomfort at least three times a month for the last 3 months without other disease or injury that could explain the pain. The pain or discomfort of IBS may occur with a change in stool frequency or consistency or be relieved by a bowel movement. IBS can be classified into four subtypes based on a subject's usual stool consistency. The four subtypes of IBS are: IBS with constipation (IBS-C), IBS with diarrhea (IBS-D), mixed IBS (IBS-M), and unsubtyped IBS (IBS-U). A subject with IBS-C may have hard or lumpy stools at least 25 percent of the time, may have loose or watery stools less than 25 percent of the time, or a combination of the two. A subject with IBS-D may have loose or watery stools at least 25 percent of the time, hard or lumpy stools less than 25 percent of the time, or a combination of the two. A subject with IBS-M may have hard or lumpy stools at least 25 percent of the time and loose or watery stools at least 25 percent of the time. A subject with IBS-U may have hard or lumpy stools less than 25 percent of the time, loose or watery stools less than 25 percent of the time, or a combination of the two. Constipation associated with IBS may be due to slow or delayed gastric motility. In some embodiments, the subject with IBS has experienced constipation. IBS can be diagnosed in a subject by any means known in the art or otherwise described herein. For instance, IBS may be diagnosed by a health care provider. The health care provider may conduct a physical exam and may take a medical history of the subject. IBS may be diagnosed if a subject has exhibited one or more symptoms of IBS for at least 3, 4, 5, or 6 months, with one or more symptoms occurring at least three times a month for the previous 3 months. Additional tests that may be useful in the diagnosis of IBS include, but are not limited to: a stool test, lower GI series, flexible sigmoidoscopy, or colonoscopy.

The subject may be suffering from, may be diagnosed with, may be exhibiting a symptom of, or may be suspected of having functional dyspepsia (e.g., impaired digestion). Symptoms of dyspepsia include, e.g., chronic or recurrent pain in the upper abdomen, upper abdominal fullness, bloating, belching, nausea, and heartburn. Functional dyspepsia (e.g., nonulcer dyspepsia) generally refers to dyspepsia without evidence of an organic disease that is likely to explain the symptoms of dyspepsia. An example of functional dyspepsia is dyspepsia in the absence of an ulcer. Functional dyspepsia is estimated to affect about 15% of the general population in western countries. Other exemplary ENS disorders include, e.g., intestinal dysmotility, ganglioneruoma, multiple endocrine neoplasia type 2B (MEN2B), gastrointestinal neuropathy, and intestinal neuronal dysplasia.

The subject may be suffering from, may be diagnosed with, may be exhibiting a symptom of, or may be suspected of having an enteric nervous system disorder caused by another underlying disease. For example, the enteric nervous system disorder can be a Parkinson's disease-induced ENS disorder. Parkinson's disease-induced ENS disorder can be related to degeneration of dopamine ENS neurons. Symptoms of a Parkinson's disease-induced ENS disorder include, e.g., constipation, nausea, vomiting, and the like. In some embodiments, a subject to be treated according to a method of the invention is diagnosed with, suffering a symptom of, is suspected of having, Parkinson's disease, and further exhibits a symptom of an ENS disorder as described herein.

The subject may be suffering from, may be diagnosed with, may be exhibiting a symptom of, or may be suspected of having an enteric nervous system disorder can associated with Scleroderma. Scleroderma can be characterized by hardening and tightening of the skin and connective tissues. In some embodiments, the subject is suffering from, may be diagnosed with, may be exhibiting a symptom of, or may be suspected of having gastroparesis associated with Scleroderma.

The subject may be suffering from, may be diagnosed with, may be exhibiting a symptom of, or may be suspected of having a diabetes-associated enteric nervous system disorder. The diabetes-associated enteric nervous system disorder can be a diabetes-associated gastroparesis. The subject may be suffering from, may be diagnosed with, may be exhibiting a symptom of, or may be suspected of having an enteric nervous system disorder associated with multiple sclerosis.

Other diseases and clinical conditions that can cause an enteric nervous system disorder such as gastroparesis include, e.g., cancer, hypothyroidism, hyperthyroidism, hyperparathyroidism, adrenal insufficiency (Addison's disease), gastric ulcer, gastritis, post-gastric surgery, such as, e.g., vagotomy (resection of the vagus nerve), antrectomy (resection of a portion of the stomach distal to the antrum of the stomach), subtotal gastrectomy (resection of a gastric tumor), gastrojejunostomy (a surgical procedure that connects two lumens of the GI tract, such as a proximal segment of stomach and a segment of the small intestine), fundoplication (a surgical procedure that wraps an upper portion of the stomach around a lower end of the esophagus), poly-myositis (a persistent inflammatory muscle disease that can cause muscle weakness), muscular dystrophy (a disease that can cause progressive muscle weakness), amyloidosis (characterized by buildup of amyloid in a tissue or organ of the subject, such as in the gastrointestinal tract), intestinal pseudo-obstruction (a condition that causes symptoms that are associated with bowel obstruction but wherein no bowel obstruction is found), dermatomyositis (a disease characterized by muscular inflammation), systemic lupus erythematosus (a systemic autoimmune disease that can affect various tissues of the body, including the nervous system), eating disorders such as, e.g., anorexia and bulimia, depression, paraneoplastic syndrome, and high cervical cord lesions (e.g., lesions at spinal cord C4 or above).

The subject can be suffering a symptom of an enteric nervous system disorder. Exemplary symptoms are described herein. In some embodiments, the symptom is nausea and/or vomiting. In some embodiments, the cause of the symptom is unknown (e.g., unexplained nausea). In some embodiments, the symptom is a chronic or recurrent symptom. The subject may, for example, experience the symptom for over 3 days, over 5 days, over 1 week, over 2 weeks, over 4 weeks, over 1 month, over 2 months, over 3 months, over 4 months, over 5 months, over 6 months, over 7 months, over 8 months, over 9 months, over 10 months, over 11 months, over 12 months (1 year), over 1.5 years, over 2 years, over 3 years, over 4 years, over 5 years, over 6 years, over 7 years, over 8 years, over 9 years, or over 10 years. The subject may experience the symptom 1, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, or more than 31 times a month.

In some embodiments, the symptom is a side effect of a drug administration and/or a treatment regimen. The treatment regimen can be a treatment regimen for cancer. Exemplary treatment regimens for cancer which are known to induce a symptom of an enteric nervous system disorder include chemotherapy. Exemplary chemotherapeutic agents which can induce nausea and/or vomiting in a subject include, but are not limited to, cisplatin, cyclophosphamide, carmustine, dicarbazine, actinomycin D, mechlorethamine, carboplatin, doxorubicin, epirubicin, irinotecan, methotrexate, and dacarbazine. In some embodiments, the administered drug causing the symptom is an anesthetic drug. The anesthetic drug can be a general anesthetic. Exemplary general anesthetic drugs include, but are not limited to, propofol, fentanyl, rocuronium, nitrous oxide, physostigmine and opioids. In some embodiments, the compounds described herein are used in the treatment of post-operative nausea and/or vomiting (PONY).

The subject may be, e.g., a mouse, a rat, a hamster, a gerbil, a dog, a cat, a primates such as, e.g., a monkey or human. In some embodiments, the subject is a human. The subject may be an adult, a child, or an infant. The subject can be of any age.

Use of the Compounds

Compounds described herein can be safely administered to a subject. Compounds described herein can be administered without necessarily increasing risk of developing a deleterious cardiac side effect. For example, compounds described herein may not increase risk of modulating cardiac action potential, and/or may not increase risk of inducing long QT syndrome, and/or may not increase risk of cardiac arrest, and/or may not increases risk of sudden death by cardiac arrest.

The subject may be safely administered an effective amount of a compound described herein for an unlimited amount of time. The subject may be safely administered an effective amount of the compound acutely or chronically. For example, the subject may be safely administered an effective amount of the compound once, for one day, for 2 days or more, for 3 days or more, for four days or more, for five days, for over five days, for over six days, for over seven days (1 week), for over 2 weeks, for over 3 weeks, for over 4 weeks, for over 5 weeks, for over 6 weeks, for over 7 weeks, for over 8 weeks, for over 9 weeks, for over 10 weeks, for over 11 weeks, for over 12 weeks, for over 3 months, for over 4 months, for over 5 months, for over 6 months, for over 7 months, for over 8 months, for over 9 months, for over 10 months, for over 11 months, for over 12 months (1 year), for over 2 years, for over 5 years, or for over a decade.

Administration of a compound described herein may confer an acceptable risk that the subject will develop an unwanted cardiac side effect. Risk of compound administration on developing such unwanted cardiac side effect can be determined by any means known in the art, or as described herein. For example, risk can be determined by comparing the incidence of sudden death in a population of subjects administered the compounds as compared to incidence of sudden death in a population of control subjects that have not been administered the compounds. Risk can be determined by tracking the number of subjects administered the compound who experienced the unwanted cardiac side effect, and the number of subjects administered the compound who did not experience the unwanted cardiac side effect. For example, if a=the number of subjects administered the compound who experienced the unwanted cardiac side effect, and b=the number of subjects administered the compound who did not experience the unwanted cardiac side effect, the risk of experiencing the unwanted cardiac side effect conferred by being administered the compound can be calculated as a/(a+b). Relative risk (RR) may be used to compare the risk of developing an unwanted cardiac side effect conferred by administration of the compound to the risk of developing the unwanted cardiac side effect in a population of subjects that have not been administered the compound. For example, if a=the number of subjects administered the compound who experienced the unwanted cardiac side effect, b=the number of subjects administered the compound who did not experience the unwanted cardiac side effect, c=the number of subjects not administered the compound who experienced the unwanted cardiac side effect, and d=the number of subjects not administered the compound who did not experience the unwanted cardiac side effect, RR conferred by administration of the compound can be calculated as a/(a+b)/(c/(c+d). For other example, risk can be determined by calculating an odds ratio.

The RR of administration of a compound described herein with sudden cardiac death can be less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

In some embodiments, the RR of administration of metopimazine with sudden cardiac death is less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

In some embodiments, the RR of administration of metopimazine acid with sudden cardiac death is less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

In some embodiments, the RR of administration of carbidopa with sudden cardiac death is less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

The odds ratio of administration of a compound described herein with sudden cardiac death can be an acceptable odds ratio. The term odds ratio (OR) generally refers to a measure of association between an exposure (e.g., exposure to a drug) and an outcome (e.g., sudden cardiac death). The OR can represent the odds that the outcome will occur given a particular exposure, as compared to the odds of the outcome occurring in the absence of that exposure. Odds ratios can be used in case-control studies, as well as in cross-sectional and cohort study design studies. For example, if a=the number of subjects administered the compound who experienced the unwanted cardiac side effect, b=the number of subjects administered the compound who did not experience the unwanted cardiac side effect, c=the number of subjects not administered the compound who experienced the unwanted cardiac side effect, and d=the number of subjects not administered the compound who did not experience the unwanted cardiac side effect, OR conferred by administration of the compound can be calculated as ad/bc.

The OR of administration of a compound described herein with sudden cardiac death can be less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

In some embodiments, the OR of administration of metopimazine with sudden cardiac death is less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

In some embodiments, the OR of administration of metopimazine acid with sudden cardiac death is less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

In some embodiments, the OR of administration of carbidopa with sudden cardiac death is less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

Unlike other dopamine modulating drugs previously indicated for the treatment of ENS, the compounds described herein for use in the treatment of ENS are peripherally restricted compounds. Accordingly, such compounds can be safely administered to a subject without increasing risk in the subject for developing motor-related dysfunction mediated by brain dopaminergic signaling. For example, such compounds can be safely administered to a subject without increasing risk in the subject for developing an extrapyramidal side effect. Exemplary extrapyramidal side effects include, e.g., tardive dyskinesia (involuntary asymmetrical movements of the muscles), dystonia (characterized by sustained muscle contractions), akinesia (lack of movement), akathisia (feeling of motor restlessness), bradykinesia (slowed movements), stiffness, and tremor, twisting and/or repetitive movements, abnormal postures, muscle spasms, e.g., muscle spasms of the neck (torticullis), muscle spasms of the eyes (oculogyric crisis) tongue spasms, spasms of the jaw, and the like. Extrapyramidal symptoms can be assessed by any means known in the art or otherwise described herein. For example, extrapyramidal symptoms may be assessed using the Simpson-Angus Scale (SAS) and/or the Barnes Akathisia Rating Scale (BARS). In some embodiments the odds ratio of administration of the compounds described herein for use in treating an enteric nervous system disorder with incidence of an extrapyramidal side effect is less than 4, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1. In some embodiments, the odds ratio of administration of metopimazine with incidence of an extrapyramidal side effect is less than 4, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1. In some embodiments, the odds ratio of administration of metopimazine acid with incidence of an extrapyramidal side effect is less than 4, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1. In some embodiments, the odds ratio of administration of carbidopa with incidence of an extrapyramidal side effect is less than 4, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

The compounds of the invention can promote gastric motility upon administration to the subject. Such compounds may promote gastric motility by, for example, reducing dopamine D2-receptor mediated signaling in an enteric neuron of the subject. For example, the metopimazine and metopimazine acid can antagonize dopamine D2 receptors in an enteric neuron of the subject. For other example, a dopamine decarboxylase inhibitor, e.g., carbidopa, can reduce peripheral dopamine synthesis and thus may reduce dopamine neurotransmission of an enteric neuron.

Gastric motility can be assessed by any means known to those of skill in the art or otherwise described herein. For example, gastric motility can be assessed by antral manometry, or by methods useful in the diagnosis of gastroparesis. Exemplary methods useful in the diagnosis of gastroparesis are described herein.

Administration of the compounds as described herein can improve gastric motility as compared to a control subject and/or control population. The control subject can be an individual that has not been administered a compound described herein. A control population can be a plurality of individuals that have not been administered a compound described herein. The control subject can be a subject that is suffering from, that has been diagnosed with, be suspected of having, or exhibiting a symptom of an ENS disorder, that is not administered a compound as described herein. The control subject does not necessarily need to be a different individual, but may be the same subject at a time point prior to receiving a dose of a compound as described herein. The control subject may be the same subject at a time point subsequent to receiving a dose of a compound as described herein, after a sufficient time has passed such that the compound is no longer acting in the subject. The control subject can be a different subject. In some embodiments, administration of a the compound increases gastric motility by at least 25%, 30%, 35%, 40%, 45%, 50%, 55%, 60%, 65%, 70%, 75%, 80%, 85%, 90%, 95%, 100%, or over 100% as compared to a control subject.

In some embodiments, administration of a compound described herein is effective in treating a symptom of an enteric nervous system disorder in the subject. Exemplary symptoms are described herein. The symptom may be selected from the group consisting of nausea, vomiting, delayed gastric emptying, diarrhea, abdominal pain, gas, bloating, gastroesophageal reflux, reduced appetite, weight loss, and constipation. In particular cases, administration of a compound described herein reduces nausea in the subject. Administration of a compound as described herein may reduce severity of any of the symptoms described herein. In some cases, administration of a compound as described herein reduces symptom severity by 1-5%, 2-10%, 5-20%, 10-30%, 20-50%, 40-70%, 50-80%, 70-90%, 80-95%, 90-100%. In some cases, administration of a compound as described herein reduces symptom severity by at least 1%, 2%, 3%, 4%, 5%, 6%, 7%, 8%, 9%, 10%, 15%, 20%, 25%, 30%, 35%, 40%, 45%, 50%, 60%, 70%, 80%, 90%, or more than 90%.

Administration of a compound as described herein may reduce frequency of onset of a symptom. In some cases, administration of a compound as described herein reduces frequency of symptom onset by 1-5%, 2-10%, 5-20%, 10-30%, 20-50%, 40-70%, 50-80%, 70-90%, 80-95%, 90-100%. In some cases, administration of a compound as described herein reduces frequency of symptom onset by at least 1%, 2%, 3%, 4%, 5%, 6%, 7%, 8%, 9%, 10%, 15%, 20%, 25%, 30%, 35%, 40%, 45%, 50%, 60%, 70%, 80%, 90%, or more than 90%. In some cases, administration of a compound as described herein reduces frequency of symptom onset to less than 1 episode a day, less than 1 episode a week, less than 2 episodes a month, less than 1 episode a month, less than 1 episode every 2 months, less than 1 episode every 3 months, less than 1 episode every 4 months, less than 1 episode every 5 months, less than 1 episode every 6 months, less than 1 episode every 7 months, less than 1 episode every 8 months, less than 1 episode every 9 months, less than 1 episode every 10 months, less than 1 episode every 11 months, or less than 1 episode every 12 months (1 year).

Exemplary Compounds

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound can be modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs can be useful because, in some situations, they may be easier to administer than the parent drug. They may, for instance, be bioavailable by oral administration whereas the parent is not. The prodrug may have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol, 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Sites on the aromatic ring portion of compounds of any of Formula I-XI can be susceptible to various metabolic reactions, therefore incorporation of appropriate substituents on the aromatic ring structures, such as, by way of example only, halogens can reduce, minimize or eliminate this metabolic pathway. Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts can be recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Any of the structures herein can encompass compounds that differ by the presence of one or more isotopically enriched atoms. For example, compounds having a structure herein, except for the substitution of one or more hydrogens by a deuterium and/or tritium are within the scope of the invention. For other example, compounds having a structure herein, except for the substitution of a one or more carbons by 13C- or 14C-enriched carbon are within scope of this invention. The compounds of the present invention may also contain unnatural portions of atomic isotopes at one or more of atoms that constitute such compounds.

Compounds utilized in embodiments of the invention may comprise a phenothiazine group, may be peripherally restricted upon administration to a subject and may not substantially inhibit an hERG channel. Compounds comprising a phenothiazine group may be referred to herein as "phenothiazines" or "phenothiazine compounds". The phenothiazine compound which is peripherally restricted upon administration to a subject and does not substantially inhibit an hERG channel may be a compound of Formula I:

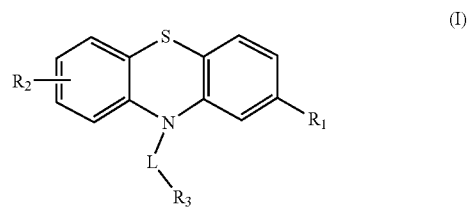

wherein $R_1$ and $R_2$ are each independently selected from the group consisting of H, cyano, nitro, azido, halo, —$CF_3$, unsubstituted $C_1$-$C_4$ alkyl, —$SR_4$, —$S(O)R_4$, —$S(O)_2R_4$, —$NR_4R_4$, —$OR_4$ and $C_1$-$C_4$ alkyl substituted with one or more substituents selected from the group consisting of halo, —$OR_4$, —$SR_4$, —$S(O)R_4$, —$S(O)_2R_4$, or —$OR_4$; each $R_4$ is independently selected from H and $C_1$-$C_4$ alkyl; L a bond or $C_1$-$C_{10}$ alkyl optionally substituted with —$OR_4$ or $NR_4R_4$; and $R_3$ is H, —$NR_4R_4$, or $C_3$-$C_7$ heterocycloalkyl having 1, 2, or 3 heteroatoms selected from N, O, and S in the ring, wherein the heterocycloalkyl group if present is optionally substituted with one or more substituents selected from the group consisting of aryl, $R_4$, —$CO_2H$, —$CO_2R_4$, —$C(O)NR_4R_4$ and $C_1$-$C_4$ alkyl optionally substituted with —$OR_4$ or —$NR_4R_4$.

The compound of Formula I may be a compound of Formula II:

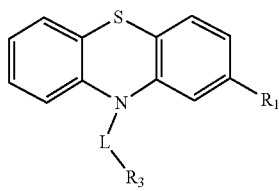

(II)

wherein $R_1$ is H, halo, —$CF_3$, unsubstituted $C_1$-$C_4$ alkyl, —$SR_4$, —$S(O)R_4$, —$S(O)_2R_4$, or —$OR_4$; each $R_4$ is independently selected from H and $C_1$-$C_4$ alkyl; L is a bond or $C_1$-$C_6$ alkyl; and $R_3$ is H, —$NR_4R_4$, or $C_3$-$C_7$ heterocycloalkyl having 1, 2, or 3 heteroatoms selected from N, O, and S in the ring, wherein the heterocycloalkyl group if present is optionally substituted with —$CO_2H$, —$CO_2R_4$, —$C(O)NR_4R_4$, or $C_1$-$C_4$ alkyl optionally substituted with —$OR_4$, —$NR_4R_4$.

In particular embodiments, the compound of Formula II is a compound of Formula III:

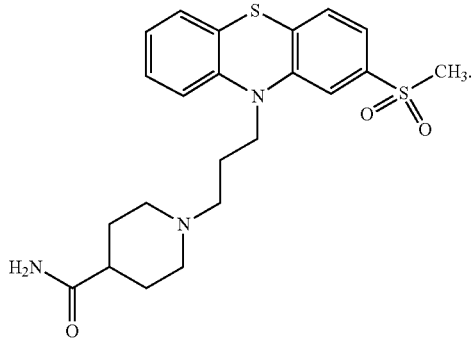

(III)

The compound of Formula III is referred to herein as "metopimazine" or 1-[3-[2-(methyl sulfonyl)-10H-phenothiazin-10-yl]propyl]-piperidine-4-carboxamide. Metopimazine, and methods of making metopimazine, are described in DE1092476, hereby incorporated by reference. Metopimazine can be obtained from a variety of commercial sources (CAS registry number 0014008-44-7). By way of example only, metopimazine can be obtained from ABI Chemicals (#AC2A05HFH), AKos (#AKOS005065914), Biochempartner (#BCP9000716), Molport (#MolPort-003-808-703), Santa Cruz Biotechnology (#sc-211901), and Tractus Company Limited (#TX-013443).

In particular embodiments, the compound of Formula II is a compound of Formula IV:

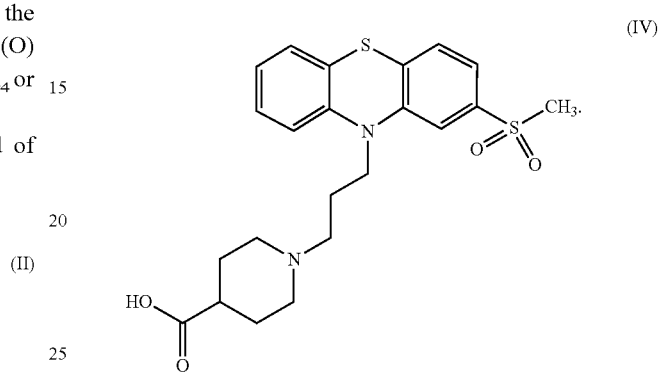

(IV)

A compound of Formula (IV) can be referred to as "metopimazine acid". Metopimazine acid can be obtained from a variety of commercial sources, such as, e.g., Santa Cruz Biotechnology, Inc., (catalog #SC211902), TLC Pharmachem (#M-363), CacheSyn (#CSTM363), and Toronto Research Chemicals (#M338767).

Also provided herein are prodrugs of metopimazine and/or metopimazine acid. Exemplary prodrugs are described herein.

Prodrugs of the invention can include ester, amide, or amino acid prodrug forms of metopimazine and/or metopimazine acid. In some embodiments, the prodrug of metopimazine acid is a compound of Formula (V):

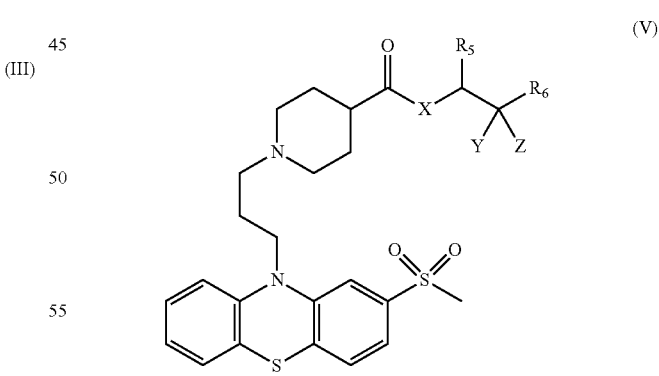

(V)

wherein X is O or NH; $R_5$ is $C_1$-$C_6$ linear or branched alkyl, benzyl, $CH_2OH$, $CH_2CH_2OH$, or $CH_2CH_2SMe$; Y and Z are both hydrogen or together can be a carbonyl oxygen; $R_6$ is OH, $OR_7$, or $NR_8R_9$; and $R_7$, $R_8$, and $R_9$ are independently $C_1$-$C_4$ linear or branched alkyl.

Alternatively, the prodrug of metopimazine acid can comprise an acetal and/or aminal moiety. For example, a prodrug of metopimazine acid can be described by formula (VI):

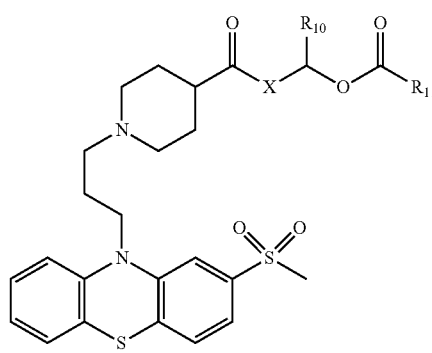

(VI)

wherein $R_{10}$ is $C_1$-$C_4$ linear or branched alkyl; and $R_{11}$ is $C_1$-$C_6$ linear or branched alkyl, phenyl, or $C_4$-$C_7$ cycloalkyl.

Alternatively, the prodrug of metopimazine acid can comprise an ester moiety. An exemplary ester prodrug of metopimazine acid is ethyl 1-[3-(2-methylsulfonylphenothiazin-10-yl)propyl]piperidine-4-carboxylate (Formula VII):

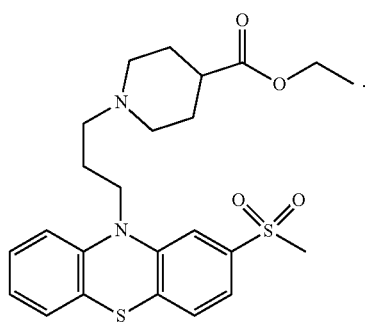

(VII)

Another exemplary ester prodrug of metopimazine acid is [2-(dimethylamino)-2-oxo-ethyl] 1-[3-(2-methylsulfonylphenothiazin-10-yl)propyl]piperidine-4-carboxylate (Formula VIII)

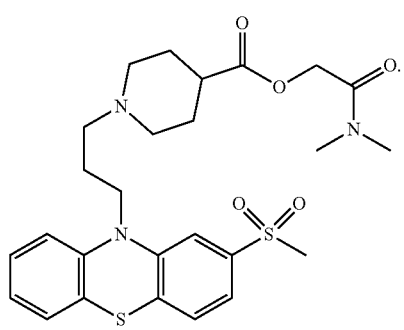

(VIII)

Yet another exemplary ester prodrug of metopimazine acid is 2-dimethylaminoethyl 1-[3-(2-methylsulfonylphenothiazin-10-yl)propyl]piperidine-4-carboxylate (Formula IX):

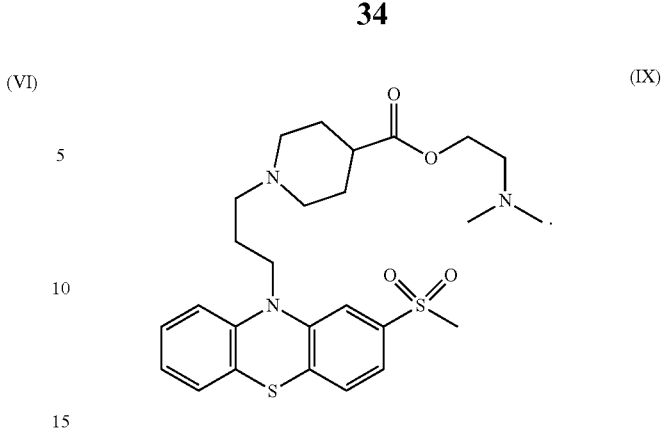

(IX)

The prodrug of metopimazine acid can comprise an amino acid moiety. An exemplary amino acid prodrug of metopimazine acid is 1-(2-methylpropanoyloxy)ethyl 1-[3-(2-methylsulfonylphenothiazin-10-yl)propyl]piperidine-4-carboxylate (Formula X):

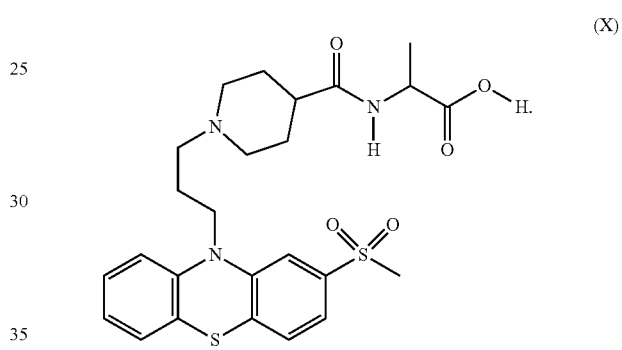

(X)

Another exemplary prodrug of metopimazine acid is 2-[[1-[3-(2-methylsulfonylphenothiazin-10-yl)propyl]piperidine-4-carbonyl]amino]propanoic acid (Formula XI):

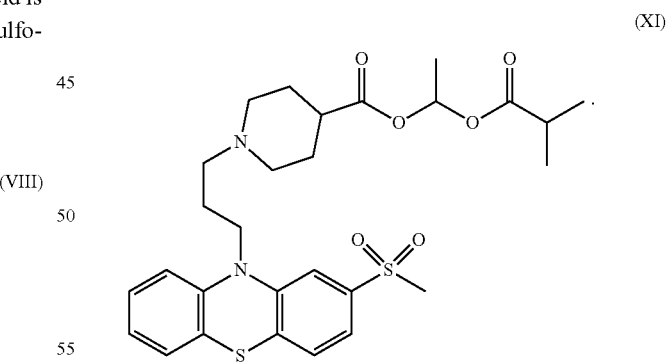

(XI)

Dopamine Decarboxylase Inhibitors

Compounds utilized in embodiments of the invention may include dopamine decarboxylase inhibitors. The dopamine decarboxylase inhibitor can be a peripherally restricted dopamine decarboxylase inhibitor. In some embodiments, the peripherally restricted dopamine decarboxylase inhibitor is carbidopa. The carbidopa may be S-carbidopa. The carbidopa may be L-carbidopa. The carbidopa may be a mixture of S-carbidopa and L-carbidopa. The IUPAC systemic name for carbidopa is (2S)-3-(3,4-dihydroxyphenyl)-2-hydrazino-2-methylpropanoic acid. Carbidopa is available from a variety of commercial vendors, such as, e.g., Aton Pharma, Inc. Pharmaceutical compositions comprising carbidopa can be manufactured by a variety of pharmaceutical companies, such as, by way of example only, Aton Pharma, Inc., Bristol-Myers Squibb Co., Medisca, Inc., and Merck & Company. In some embodiments, the peripherally restricted dopamine decarboxylase inhibitor is Benserazide, Methyldopa, or α-Difluoromethyl-DOPA (DFMD, DFM-DOPA). Pharmaceutical compositions comprising Benserazide can be manufactured by a variety of pharmaceutical companies, such as, by way of example only, Roche. Pharmaceutical compositions comprising methyldopa can be manufactured by a variety of pharmaceutical companies, such as, by way of example only, Merck and Company. α-Difluoromethyl-DOPA is described in Journal of Neurochemistry 31(4):927-932, which is hereby incorporated by reference in its entirety.

Peripherally Restricted Dopamine D2 Receptor Antagonists

Compounds utilized in embodiments of the invention may include peripherally restricted D2 receptor antagonists which exhibit minimal hERG channel inhibition. Compounds may be identified as being dopamine D2 receptor antagonists by any means known in the art, or otherwise described herein. In some cases, a compound can be identified as a D2 receptor antagonist via a functional antagonist assay. A typical functional antagonist assay measures the ability of a putative antagonist to inhibit receptor signaling mediated by an agonist. For example, a compound can be identified as a D2 receptor antagonist if the compound inhibits D2 receptor-mediated signaling. Exemplary D2 receptor-mediated signaling events include, but are not limited to, cAMP signaling, ERK phosphorylation, and β-arrestin translocation. Such D2 receptor-mediated signaling events can be assayed using methods known in the art. For example, D2 receptor-mediated cAMP signaling can be assessed using the GloSensor™ cAMP Assay (Promega, Inc.). For other example, D2 receptor-mediated ERK phosphorylation can be determined by, e.g., western blot analysis. In some cases, a compound can be identified as a D2 receptor antagonist via radioligand binding assay. In some embodiments, the dopamine D2 receptor antagonist is not domperidone. In some embodiments, the dopamine D2 receptor antagonist is not a compound of Formula (Y):

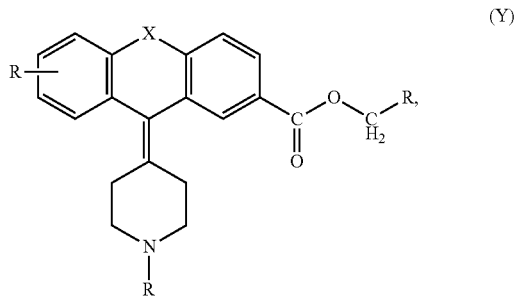

wherein X is —CH=CH—, —CH$_2$—CH$_2$—, —CH$_2$—O—, —O—CH$_2$—, —S—CH$_2$—, CH$_2$—S—, —S—, or —O—, and R is a 5- or 6-membered nitrogen heterocyclic ring optionally fused to a benzo group.

The D2 receptor antagonist utilized in a method of the invention can have a potency. The potency can be defined by its IC50 value, which denotes the concentration of antagonist needed to elicit half inhibition of the maximum biological response of an agonist. In some embodiments, the IC50 of the dopamine D2 receptor antagonist is $10^{-12}$ M to $10^{-5}$ M. In some embodiments, the dopamine D2 receptor antagonist is a D2/D3 receptor antagonist.

A D2 receptor antagonist can be identified as a peripherally restricted molecule (e.g., as not crossing an intact blood brain barrier) by any means known in the art or otherwise described herein. For example, a labeled compound may be administered peripherally to a subject, and monitored for detection of the labeled compound in a forebrain or midbrain brain tissue. Detection of the labeled compound in a forebrain or midbrain brain tissue can be determined by ex vivo and/or in vivo methods known to those of skill in the art, such as, by way of non-limiting example, PET imaging, immunohistochemistry, radioligand binding, and the like. For other example, capability of a molecule to cross a blood brain barrier can be determined by an in vitro assay. An exemplary in vitro assay is described in U.S. Pat. No. 8,417,465, which is hereby incorporated by reference.

hERG channel inhibition can be determined by any means known in the art or otherwise described herein. hERG channel inhibition can be assessed in vitro, for example, by utilizing hERG expressing cultured cells. hERG-expressing cultured cells for the purposes of assessing hERG channel inhibition are available from a number of commercial vendors, such as, e.g., Life Technologies, Cyprotex, and the like. hERG channel inhibition can be assessed by a variety of means known in the art, including, e.g., voltage clamp studies, hERG binding assays, and the like. Voltage clamp studies can employ the use of commercially available high throughput systems. Exemplary high-throughput systems are described in, e.g., U.S. Pat. No. 8,329,009, and US Patent Application Pub. No. 20020164777, which are hereby incorporated by reference. hERG binding assays can include competition and/or saturation binding assays using $^{3H}$dofetilide. Such assays are described in J Pharmacol Toxicol Methods. 2004 November-December; 50(3):187-99, which is hereby incorporated by reference. hERG channel inhibition can be determined by in vivo studies, for example, by assessment of cardiac action potentials in large animal models, e.g., canines.

Minimal hERG inhibition can be evidenced by an IC50 that is higher than 0.1 μM, higher than 0.2 μM, higher than 0.3 μM, higher than 0.4 μM, higher than 0.5 μM, higher than 0.6 μM, higher than 0.7 μM, higher than 0.8 μM, higher than 0.9 μM, higher than 1 μM, higher than 2 μM, higher than 3 μM, higher than 4 μM, higher than 5 μM, higher than 6 μM, higher than 7 μM, higher than 8 μM, higher than 9 μM, higher than 10 μM, higher than 15 μM, higher than 20 μM, higher than 30 μM, higher than 40 μM, higher than 50 μM, higher than 60 μM, higher than 70 μM, higher than 80 μM, higher than 90 μM, or higher than 100 μM.

Minimal hERG inhibition can also be evidenced by measuring, at any given dose of a drug, the % inhibition of hERG-mediated tail current. hERG-mediated tail current can be measured by voltage clamp studies, e.g., by patch clamps studies. For example, hERG-mediated tail current can be measured in an hERG-expressing cell prior to contact of the cell with a test agent. hERG-mediated tail current can then be measured in the hERG-expressing cell after contact with a dose of the test agent. The differences between the hERG-mediated tail current before and after administration of the test agent can be used to determine the extent to which the test agent inhibited hERG-mediated tail current. A suitable agent for use in the invention can, at a 1 μM dose, inhibit hERG-mediated tail current by less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%. A suitable agent for use in the invention can, at a 100 nM dose, inhibit hERG-mediated tail current by less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%. In some embodiments, metopimazine can, at a 3 µM dose, inhibit hERG-mediated tail current by less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%. In some embodiments, metopimazine acid can, at a 10 µM dose or higher, inhibit hERG-mediated tail current by less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%.

Exemplary Pharmaceutical Compositions

In general, the methods of the invention utilize pharmaceutical compositions comprising one or more of the compounds described herein for the treatment of an enteric nervous system disorder. In some embodiments, the pharmaceutical composition comprises a compound of Formula I. In some embodiments, the pharmaceutical composition comprises a compound of Formula II. In some embodiments, the pharmaceutical composition comprises a compound of Formula III. In some embodiments, the pharmaceutical composition comprises a compound of Formula IV. In some embodiments, the pharmaceutical composition comprises a compound of any of Formulas V-XI. In some embodiments, the pharmaceutical composition comprises carbidopa. In some embodiments, the pharmaceutical composition comprises a peripherally restricted dopamine D2 receptor antagonist that does not inhibit hERG activity. In some embodiments, the composition comprises a therapeutically effective amount of any of the compounds described herein for the treatment of an enteric nervous system disorder.

Pharmaceutical compositions utilized in the methods of the invention may include a pharmaceutically acceptable carrier. The pharmaceutically acceptable carrier for the present compositions may include, but are not limited to, amino acids, peptides, biological polymers, non-biological polymers, simple sugars or starches, inorganic salts, and gums, which may be present singly or in combinations thereof. The peptides used in the acceptable carrier may include, e.g., gelatin and/or albumin. Cellulose or its derivatives may be used in the pharmaceutically acceptable carrier. The sugar used in the acceptable carrier may be lactose and/or glucose. Other useful sugars which may be utilized in the pharmaceutical compositions include but are not limited to, fructose, galactose, lacticol, maltitol, maltose, mannitol, melezitose, myoinositol, palatinate, raffinose, stachyose, sucrose, tehalose, xylitol, hydrates thereof, and combinations of thereof. Binders may be included in the pharmaceutically acceptable carrier. Examples of binders include, but are not limited to, starches (for example, corn starch or potato starch), gelatin; natural or synthetic gums such as acacia, sodium alginate, powdered tragacanth, guar gum, cellulose or cellulose derivatives (for example, methylcellulose, ethyl cellulose, cellulose acetate); microcrystalline cellulose, polyvinyl pyrrolidone, and mixtures thereof. Inorganic salts used in the acceptable carrier may be a magnesium salt, for example, magnesium chloride or magnesium sulfate. Other inorganic salts may be used, for example, calcium salts. Examples of calcium salts include, but are not limited to, calcium chloride, calcium sulfate. Other examples of substances which may be used in the pharmaceutically acceptable carrier include, but are not limited to, vegetable oils, such as peanut oil, cottonseed oil, olive oil, corn oil; polyols such as glycerin, propylene glycol, polyethylene glycol; pyrogen-free water, isotonic saline, phosphate buffer solutions; emulsifiers, such as the Tweens®; wetting agents, lubricants, coloring agents, flavoring agents, preservatives.

The term "wetting agents" may be used interchangeably with "surfactants", and refers to substances that lower the surface tension of a liquid, thus allowing the liquid to spread more easily. Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. A useful parameter that may be used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are generally considered to be compounds having an HLB value equal to or less than about 10. However, HLB value of a surfactant merely provides a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts, fatty acid derivatives of amino acids, glyceride derivatives of amino acids, fusidic acid salts, oligopeptides, and polypeptides, oligopeptides, and polypeptides, lecithins and hydrogenated lecithins, lysolecithins and hydrogenated lysolecithins, phospholipids and derivatives thereof, fatty acid salts, lysophospholipids and derivatives thereof, carnitine fatty acid ester salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Within the aforementioned group, ionic surfactants include, but are not limited to, lecithins, lysolecithin, phospholipids, lysophospholipids and derivatives thereof, carnitine fatty acid ester salts, fatty acid salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Ionic surfactants may be the ionized forms of lactylic esters of fatty acids, lecithin, lysolecithin, phosphatidylethanolamine, phosphatidylcholine, phosphatidylglycerol, phosphatidic acid, phosphatidylserine, lysophosphatidylcholine, lysophosphatidylserine, lysophosphatidylethanolamine, lysophosphatidylglycerol, lysophosphatidic acid, PEG-phosphatidylethanolamine, PVP-phosphatidylethanolamine, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, linoleate, linolenate, stearate, ricinoleate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides, alkylthioglucosides, alkylmaltosides, lauryl macrogolglycerides, polyoxyalkylene alkyl ethers such as polyethylene glycol alkyl ethers, polyoxyalkylene alkylphenols such as polyethylene glycol alkyl phenols, polyethylene glycol glycerol fatty acid esters, polyoxyalkylene alkyl phenol fatty acid esters such as polyethylene glycol fatty acids monoesters and polyethylene glycol fatty acids diesters, polyglycerol fatty acid esters, polyoxyethylene-polyoxypropylene block copolymers and mixtures thereof, polyoxyalkylene sorbitan fatty acid esters such as polyethylene glycol sorbitan fatty acid esters, hydrophilic transesterification products of a polyol with at least one member of the group consisting of glycerides, vegetable oils, hydrogenated vegetable oils, fatty acids, and sterols, polyoxyethylene sterols and derivatives or analogues thereof, polyoxyethylated vitamins and derivatives thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-12 oleate, PEG-15 oleate, PEG-20 oleate, PEG-20 laurate, PEG-32 dilaurate, PEG-32 laurate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-20 trioleate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-50 hydrogenated castor oil, PEG-40 castor oil, PEG-35 castor oil, PEG-60 castor oil, PEG-40 palm kernel oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, but are not limited to, fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar ethers, sugar esters, hydrophobic transesterification products of a polyol with at least one member of the group consisting of glycerides, vegetable oils, hydrogenated vegetable oils, fatty acids and sterols, oil-soluble vitamins/vitamin derivatives, lactic acid derivatives of mono- and di-glycerides, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Lubricants that may be used in the pharmaceutical composition include, but are not limited to, agar, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, or mixtures thereof. Additional lubricants include, by way of example, a syloid silica gel, a coagulated aerosol of synthetic silica, or mixtures thereof. A lubricant can optionally be added, in an amount of less than about 1 weight percent of the pharmaceutical composition.

The composition may include a solubilizer to ensure good solubilization of the compound and to reduce precipitation of the compound of the present invention. A solubilizer may be used to increase solubility of the compound or other active ingredients, or may be used to maintain the composition as a homogeneous solution or dispersion. Examples of suitable solubilizers include but are not limited to, alcohols and polyols such as ethanol, isopopropanol, polyvinyl alcohol, gelatin, mannitol, sodium carboxymethyl cellulose (CMCNa), povidone, propylene glycol, polyethylene glycol, polyvinyl pyrolidone, glycerin, cyclodextrins or cyclodextrin derivatives, polyethylene glycol ethers of molecular weight averaging about 200 to about 6000, such as PEG, amides and other nitrogen-containing compounds such as 2-pyrrolidone, 2-piperidone, epsilon-caprolactam, N-alkylpyrrolidone, N-hydroxyalkylpyrrolidone, N-alkylpiperidone, N-alkylcaprolactam, dimethylacetamide and polyvinylpyrrolidone, esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, water, or mixtures and/or combinations thereof.

Mixtures of solubilizers may also be used. Examples of solubilizers include, but not limited to, ethyl oleate, ethyl caprylate, triacetin, triethylcitrate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, transcutol, propylene glycol, glycofurol and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example, to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 75%, 100%, or up to about 200% by weight, based on the combined weight of the drug, and other excipients. If desired, very small amounts of solubilizer may also be used, such as 5%, 2%, 1%, 0.5% or even less. Typically, the solubilizer may be present in an amount of about 1% to about 100%, more typically about 5% to about 25% by weight.

The composition may include one or more pharmaceutically acceptable additives, which may include, but are not limited to, detackifiers, anti-foaming agents, buffering agents, antioxidants, polymers, preservatives, chelating agents, odorants, opacifiers, suspending agents, fillers, plasticizers, and mixtures thereof.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the concentration of the compound is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09%, to about 22%, about 0.1% to about 21%, about 0.2% to about 20%, about 0.3% to about 19%, about 0.4% to about 18%, about 0.5% to about 17%, about 0.6% to about 16%, about 0.7%, to about 15%, about 0.8% to about 14%, about 0.9% to about 12%, about 1% to about 10% of the pharmaceutical composition by w/w, w/v or v/v.

In some embodiments, the concentration of the compound is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v.

In some embodiments, the amount of the compound in the pharmaceutical composition is about 0.00001 mg, 0.0001 mg, 0.001 mg, 0.005 mg, 0.01 mg, 0.05 mg, 0.1 mg, 0.25 mg, 0.5 mg, 1 mg, 2 mg, 4 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.1 g, 1.2 g, 1.3 g, 1.4 g, 1.5 g, 1.6 g, 1.7 g, 1.8 g, 1.9 g, 2 g, 2.5 g, 3 g, 3.5 g, 4 g, 4.5 g, 5 g, 6 g, 7 g, 8 g, 9 g, or 10 g.

Described below are some non-limiting examples of pharmaceutical compositions.

Pharmaceutical Compositions for Oral Administration

The pharmaceutical composition comprising an effective amount of a compound can be formulated for oral administration. In some embodiments, the pharmaceutical composition comprising an effective amount of a compound for oral administration is a solid pharmaceutical composition. In some embodiments, the solid pharmaceutical composition may be presented as discrete (e.g., unit) oral dosage forms. Non-limiting examples of discrete oral dosage forms include tablets, capsules, caplets, gelatin capsules, sustained release formulations, lozenges, thin films, lollipops, chewing gum. In some embodiments, the discrete oral dosage form is an orally disintegrating oral dosage form, such as, e.g., an orally disintegrating tablet.

Discrete oral dosage forms such as tablets may be coated by known techniques to delay or prolong absorption in the gastrointestinal tract, thus providing a sustained action of a longer period of time. In some embodiments, the compound is mixed with one or more inert solid diluents, such as calcium carbonate or calcium phosphate. In some embodiments, the compound are presented as soft gelatin capsules, wherein the compound is mixed with water or an oil medium, such as peanut oil, or olive oil, for example.

In some embodiments, the pharmaceutical composition comprising an effective amount of a compound for oral administration is a liquid pharmaceutical composition. Non-limiting examples of liquid compositions for oral administration include hydrophilic suspensions, emulsions, liquids, gels, syrups, slurries, solutions, elixirs, softgels, tinctures, and hydrogels. In some embodiments, solid or liquid compositions comprising an effective amount of a compound for oral administration comprise various sweetening or flavoring agents, or coloring agents. Examples of coloring agents include dyes suitable for food such as those known as F.D. & C. dyes and natural coloring agents such as grape skin extract, beet red powder, beta carotene, annato, carmine, turmeric, paprika, and so forth. Derivatives, analogues, and isomers of any of the above colored compound also may be used.

Such dosage forms may be prepared by methods well known to those skilled in the art, e.g., in a pharmacy. Such methods would comprise bringing the compound into association with the pharmaceutically acceptable carrier.

This invention further encompasses anhydrous pharmaceutical compositions and dosage forms comprising an effective amount of a compound, since water may facilitate the degradation of the compounds. In some embodiments, the anhydrous pharmaceutical compositions and dosage forms of the invention are prepared using anhydrous or low moisture containing ingredients. In some embodiments, the anhydrous pharmaceutical compositions and dosage forms of the invention are prepared under low humidity or low moisture conditions. The pharmaceutical compositions of the present invention which contain lactose may be made anhydrous if substantial contact with moisture and/or humidity during manufacturing, packaging, and/or storage is expected. An anhydrous pharmaceutical composition comprising an effective amount of a compound may be prepared and stored such that its anhydrous nature is maintained. For example, the anhydrous compositions may be packaged using materials known to prevent exposure to water such that they can be included in suitable formulary kits, examples of which include, but are not limited to, hermetically sealed foils, plastic or the like, unit dose containers, blister packs, and strip packs.

Pharmaceutical Compositions for Injection or Parenteral Administration

In some embodiments, the pharmaceutical composition is formulated for parenteral administration. "Parenteral administration" generally refers to routes of administration other than the gastro-intestinal tract. Examples of parenteral administration include, but are not limited to, intravenous injection, intra-arterial injection, intrathecal injection (into the spinal cord), intratonsillary injection, subcutaneous injection, intramuscular injection, infusion, or implantation. Infusion may be intradermal, or subcutaneous, or through a transdermal implant. Exemplary pharmaceutical compositions for parenteral administration are disclosed in the following references which are hereby incorporated by reference: U.S. Patent Application Pub. No. 2006/0287221, U.S. Pat. Nos. 5,244,925, 4,309,421, 4,158,707, and 5,164,405, all of which are hereby incorporated by reference.

Compositions formulated for parenteral administration may include aqueous solutions and/or buffers commonly used for injection and/or infusion. Commonly used aqueous buffers and/or solutions may include, but are not limited to sodium chloride solutions of about 0.9%, phosphate buffers, Lactated Ringer's solution, Acetated ringer's solution, phosphate buffered saline, citrate buffers, Tris buffers, histidine buffers, HEPES buffers, glycine buffers, N-glycylglycine buffers, and the like. Other pharmaceutically acceptable carriers for parenteral administration may include ethanol, glycerol, propylene glycol, cyclodextrin and cyclodextrin derivatives, vegetable oils, and the like.

In some embodiments, pharmaceutical compositions for injection and/or infusion contain preservatives present in amounts that effectively prevent or reduce microbial contamination or degradation. Various agents, e.g., phenol, m-cresol, benzyl alcohol, parabens, chlorobutanol, methotrexate, sorbic acid, thimerosol, ethyl hydroxybenzoate, bismuth tribromophenate, methyl hydroxybenzoate, bacitracin, propyl hydroxybenzoate, erythromycin, 5-fluorouracil, doxorubicin, mitoxantrone, rifamycin, chlorocresol, benzalkonium chlorides, may be used to prevent or reduce contamination.

In some embodiments, sterile solutions are prepared by incorporating the compound of in the required amount in the appropriate solvent with various other ingredients as described herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain methods of preparation include but are not limited to vacuum-drying and freeze-drying techniques which yield a powder of the active ingredient plus any additional desired ingredient from a previously sterile-filtered solution thereof.

In some embodiments, the pharmaceutical composition is formulated for topical and/or transdermal delivery. Compositions of the present invention can be formulated into preparations in liquid, semi-solid, or solid forms suitable for local or topical administration. Examples of forms suitable for topical or local administration include but are not limited to, gels, water soluble jellies, creams, lotions, suspensions, foams, powders, slurries, ointments, oils, pastes, suppositories, solutions, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition may comprise suitable solid or gel phase carriers, which are compounds that allow increased penetration of, or assist in the delivery of, therapeutic molecules across the stratum corneum barrier of the skin. There are many of these penetration-enhancing molecules known to those skilled in the art of topical formulation. Examples of such carriers and excipients include, but are not limited to, alcohols (e.g., ethanol), fatty acids (e.g., oleic acid), humectants (e.g., urea), glycols (e.g., propylene glycol), surfactants (e.g., isopropyl myristate and sodium lauryl sulfate), glycerol monolaurate, sulfoxides, pyrrolidones, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound as described herein in controlled amounts, either with or without an additional agent. The construction and use of transdermal patches for the delivery of pharmaceutical agents is well known in the art. See, e.g., U.S. Pat. Nos. 5,023,252; 4,992,445; and 5,001,139; which are herein incorporated by reference.

In some embodiments, the invention provides a pharmaceutical composition comprising an effective amount of a compound as described herein for transdermal delivery, and a pharmaceutical excipient suitable for delivery by inhalation. Compositions for inhalation include solutions and suspensions in pharmaceutically acceptable, aqueous or organic solvents, or mixtures thereof, and powders. The liquid or solid compositions may contain suitable pharmaceutically acceptable excipients as described herein. The compositions may be administered by the oral or nasal respiratory route for systemic effect. In some embodiments, compositions in preferably pharmaceutically acceptable solvents may be nebulized by use of inert gases. In some embodiments, nebulized solutions may be inhaled directly from the nebulizing device. In other embodiments, nebulizing device may be attached to a face mask tent or intermittent positive pressure breathing machine. Solution, suspension, or powder compositions may be administered, preferably orally or nasally, from devices that deliver the formulation in an appropriate manner.

Other Pharmaceutical Compositions.

The pharmaceutical compositions employed in the present invention may be formulated for intraocular (ophthalmic), rectal, sublingual, buccal, or intranasal (e.g., intrapulmonary) administration. Formulations suitable for intraocular administration include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w. Formulations suitable for sublingual administration, typically are formulated to dissolve rapidly upon placement in the mouth, allowing the active ingredient to be absorbed via blood vessels under the tongue. Exemplary sublingual formulations include, e.g., lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; orally disintegrating tablets which may, for example, disintegrate in less than 90 seconds upon placement in the mouth; and thin films. Such disintegration can be measured by an in vitro dissolution test. Formulations for buccal administration can include, e.g., buccal tablets, bioadhesive particles, wafers, lozenges, medicated chewing gums, adhesive gels, patches, films, which may be delivered as an aqueous solution, a paste, an ointment, or aerosol, to name a few. Formulations for rectal administration may be presented as a suppository with a suitable base comprising for example cocoa butter or a salicylate. Formulations suitable for intrapulmonary or nasal administration can have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of cancerous infections as described below. A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Preparations for such pharmaceutical compositions are described in, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Exemplary Modes of Administration

Administration of a pharmaceutical composition as described herein can be performed by any method that enables delivery of the compound to the site of action. The composition may be administered orally, parenterally, enterally, intraperitoneally, topically, transdermally, ophthalmically, intranasally, locally, non-orally, via spray, subcutaneously, intravenously, intratonsillary, intramuscularly, buccally, sublingually, rectally, intra-arterially, by infusion, or intrathecally. In some embodiments, the composition is administered orally. In some cases, the oral administration may comprise administration of any of the oral dosage forms as described herein. The effective amount of a compound administered will be dependent on the subject being treated, the severity of the disorder or condition, the rate of administration, the disposition of the compound and the discretion of the prescribing physician.

A subject can be administered a daily dosage of a compound as described herein for the treatment of an enteric nervous system disorder. The daily dosage can be from about 0.01 mg/kg to about 500 mg/kg of body weight per day. A daily dosage for a human can be about 1, 2, 3, 4, 5, 6, 7, 8, 9, 0, 12, 14, 16, 18, 20, 25, 30, 35, 40, 45, 50, 55, 60, 65, 70, 75, 80, 90, 100, 120, 140, 160, 180, 200, 300, 400, 500, 600, 700, 800, 900, or 1000 mg. In some embodiments, the daily dosage is greater than 30 mg/day, greater than 35 mg/day, greater than 40 mg/day, greater than 45 mg/day, greater than 50 mg/day, greater than 55 mg/day, greater than 60 mg/day, greater than 65 mg/day, greater than 70 mg/day, greater than 75 mg/day, greater than 80 mg/day, greater than 85 mg/day, greater than 90 mg/day, greater than 95 mg/day, greater than 100 mg/day, greater than 150 mg/day, greater than 200 mg/day, greater than 300 mg/day, greater than 400 mg/day, greater than 500 mg/day, greater than 600 mg/day, greater than 700 mg/day, greater than 800 mg/day, greater than 900 mg/day, or greater than 1000 mg/day. A daily dosage of metopimazine for a human can be, for example, greater than 30 mg/day, greater than 35 mg/day, greater than 40 mg/day, greater than 45 mg/day, greater than 50 mg/day, greater than 55 mg/day, greater than 60 mg/day, greater than 65 mg/day, greater than 70 mg/day, greater than 75 mg/day, greater than 80 mg/day, greater than 85 mg/day, greater than 90 mg/day, greater than 95 mg/day, greater than 100 mg/day, greater than 150 mg/day, greater than 200 mg/day, greater than 300 mg/day. A daily dosage of metopimazine acid for a human can be, for example, greater than 30 mg/day, greater than 35 mg/day, greater than 40 mg/day, greater than 45 mg/day, greater than 50 mg/day, greater than 55 mg/day, greater than 60 mg/day, greater than 65 mg/day, greater than 70 mg/day, greater than 75 mg/day, greater than 80 mg/day, greater than 85 mg/day, greater than 90 mg/day, greater than 95 mg/day, greater than 100 mg/day, greater than 150 mg/day, greater than 200 mg/day, greater than 300 mg/day, greater than 400 mg/day, greater than 500 mg/day, greater than 600 mg/day, greater than 700 mg/day, greater than 800 mg/day, greater than 900 mg/day, or greater than 1000 mg/day. A daily dosage of a peripherally restricted dopamine carboxylase inhibitor (e.g., carbidopa) for a human can be, for example, greater than 30 mg/day, greater than 35 mg/day, greater than 40 mg/day, greater than 45 mg/day, greater than 50 mg/day, greater than 55 mg/day, greater than 60 mg/day, greater than 65 mg/day, greater than 70 mg/day, greater than 75 mg/day, greater than 80 mg/day, greater than 85 mg/day, greater than 90 mg/day, greater than 95 mg/day, or greater than 100 mg/day. In some embodiments, the daily dosage is 30-50 mg/day, 40-60 mg/day, 50-80 mg/day, 80-90 mg/day, 70-100 mg/day, 90-150 mg/day, 100-200 mg/day, 150-300 mg/day, or 200-500 mg/day. The compound can be administered in one or more unit dosage forms and can also be administered one to ten, one to eight, one to six, one to four, one to two times daily, or one time daily. For example, the compound can be administered four times daily. A unit dosage form can comprise about 0.1, 0.2, 0.3, 0.4, 0.5, 0.6, 0.7, 0.8, 0.9, 1, 2, 3, 4, 5, 6, 7, 8, 9, 0, 12, 14, 16, 18, 20, 25, 30, 35, 40, 45, 50, 55, 60, 65, 70, 75, 80, 90, 100, 120, 140, 160, 180, 200, 300, 400, 500, 600, 700, 800, 900, or 1000 mg of the compound.

In some embodiments, administration may comprise infusion. In some cases, infusion may involve chronic, steady dosing. Devices for chronic, steady dosing, e.g., by a controlled pump, are known in the art, (examples may be described in U.S. Pat. Nos. 7,341,577, 7,351,239, 8,058,251, herein incorporated by reference).

Administration of the compound may continue as long as necessary. In some embodiments, the compound is administered for more than 1, 2, 3, 4, 5, 6, 7, 14, or 28 days. In particular embodiments, the compound is administered for more than 5 days. In some embodiments, the compound is administered for more than 12 weeks. In some embodiments, the compound is administered for more than 1 month, more than 2 months, more than 4 months, more than 6 months, more than 1 year, more than 2 years, or more than 5 years. In some embodiments, the compound is administered for less than five days.

Exemplary Combination Therapies

In some embodiments, the method comprises co-administration of an additional agent. Additional agents may be: small molecules, nutraceuticals, vitamins, e.g., vitamin D, drugs, pro-drugs, biologics, peptides, peptide mimetics, antibodies, antibody fragments, cell or tissue transplants, vaccines, polynucleotides, DNA molecules, RNA molecules, (i.e.-siRNA, miRNA), antibodies conjugated to drugs, toxins, fusion proteins. Agents may be delivered by vectors, including but not limited to: plasmid vectors, viral vectors, non-viral vectors, liposomal formulations, nanoparticle formulations, toxins, therapeutic radioisotopes, etc.

In some embodiments, a method of the invention comprises co-administration of a peripherally restricted dopamine decarboxylase inhibitor and a compound of any of Formulas I-XI. For example, an invention method may comprise co-administration of carbidopa and a compound of any of Formulas I-IV. In some cases, an invention method comprises co-administration of carbidopa and a compound of Formula III or IV. In some cases, an invention method comprises co-administration of carbidopa and a compound of Formula III. In some cases, an invention method comprises co-administration of carbidopa and a compound of Formula IV. In some cases, an invention method comprises co-administration of carbidopa and a compound of any of Formulas V-XI. Also contemplated in the invention is a method comprising co-administration of a peripherally restricted dopamine decarboxylase inhibitor and a peripherally restricted dopamine D2 receptor antagonist that exhibits minimal hERG inhibition.

The additional agent can be an agent for use in the treatment of an enteric nervous system disorder. In some embodiments, the additional agent is an additional anti-emetic agent (e.g., used for the treatment of nausea and/or vomiting). The additional anti-emetic agent can be, by way of non-limiting example only, a 5-HT3 receptor antagonist, a dopamine receptor antagonist, an NK1 receptor antagonist, an antihistamine, a cannabinoid, a benzodiazepine, an anticholinergic agent, a steroid, or other anti-emetic. Exemplary 5-HT3 receptor antagonists include, but are not limited to, Odansetron, Tropisetron, Granisetron, Palonosetron, Dolasetron, and Metoclopramide. Exemplary dopamine receptor antagonists include, e.g., Domperidone (Motilium), Olanzapine (Zyprexa) Droperidol, haloperidol, chlorpromazine, promethazine, prochlorperazine, Alizapride, Prochlorperazine, Sulpiride, and Metoclopramide. Exemplary NK1 receptor antagonists include, e.g., Aprepitant, or Casopitant. Exemplary antihistamines include, e.g., Cyclizine, Diphenhydramine (Benadryl), Dimenhydrinate (Gravol, Dramamine), Doxylamine, Meclozine (Bonine, Antivert), Promethazine (Pentazine, Phenergan, Promacot), and Hydroxyzine (Vistaril). Exemplary cannabinoids include, e.g., Cannabis, Sativex, tetrahydrocannabinol, Dronabinol, and synthetic cannabinoids such as Nabilone. Exemplary benzodiazepines include, e.g., midazolam or lorazepam. Exemplary anticholinergic agents include, e.g., scopolamine. Other exemplary anti-emetics include, e.g., Trimethobenzamide, Ginger, Emetrol, Propofol, Peppermint, erythromycin, Muscimol, botulinum toxin A (e.g., injected into the stomach to relax the pyloric muscle), and Ajwain.

The additional agent can be an agent for treatment of another disease or clinical syndrome associated with gastroparesis. Exemplary other diseases and clinical syndromes are described herein. The additional agent can be an agent for treatment of diabetes. Exemplary agents for the treatment of diabetes include, e.g., insulin. Other agents for the treatment of diabetes are described in, for example, U.S. Pat. Nos. 6,274,549, 8,349,818, 6,184,209, US Patent Application Publication No. US20070129307, and PCT Application Publication No. WO/2004/082667A1, all of which are hereby incorporated by reference.

The additional agent can be for treatment of upper and lower dysmotility disorders associated with Parkinson's disease. The additional agent can be for treatment of Parkinson's disease. Exemplary agents for the treatment of Parkinson's disease include, e.g., dopaminergic agents, MAO-A or B inhibitors such as, e.g., selegiline, COMT inhibitors such as entacapone, amantadine, stem cell transplant, and neuroprotective agents. Exemplary dopaminergic agents include, but are not limited to levodopa, bromocriptine, pergolide, pramipexole, cabergoline, ropinorole, apomorphine or a combination thereof.

The additional agent can be for treatment of hypothyroidism, hyperthyroidism, or hyperparathyroidism. Exemplary agents for the treatment of such diseases include, e.g., beta-adrenergic blockers ("beta blockers"), levothyroxine calcimimetics, estrogen, progesterone, bisphosphonates.

The additional agent can be for treatment of adrenal insufficiency. Exemplary agents for treatment of adrenal insufficiency include, e.g., corticosteroid hormones (for example, aldosterone, fludrocortisones, and cortisol).

The additional agent can be for treatment of gastroesophageal reflux. Exemplary agents for treatment of gastroesophageal reflux include, e.g., antacids such as, for example, proton pump inhibitors such as omeprazole, H2 receptor antagonists such as ranitidine, antacids, mosapride, sucralfate, and baclofen.

The additional agent can be for treatment of scleroderma. For example, the additional agent can be D-penicillamine, colchicine, PUVA, relaxin, cyclosporine, and EPA (omega-3 oil derivative), immunosupressants such as, e.g., methotrexate, cyclophosphamide, azathioprine, and mycophenolate. The additional agent can be for treatment of polymyositis. For example, the additional agent can be a corticosteroid, e.g., prednisone, or can be an immunosuppressant.

The additional agent can be for treatment of muscular dystrophy. For example, the additional agent can be, e.g., a glucocorticoid receptor antagonist. Exemplary glucocorticoid receptor antagonists include, but are not limited to, mifepristone, 11β-(4-dimethylaminoethoxyphenyl)-17α-propynyl-17β-hydroxy-4,9 estradien-3-one, 17β-hydroxy-17α-19-(4-methylphenyl)androsta-4,9(11)-dien-3-one, 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol, and (11β,17β)-11-(1,3-benzodioxo-5-yl)-17-hydroxy-17-(1-propynyl)estra-4,9-dien-3-one.

The additional agent can be for treatment of amyloidosis. For example, the additional agent can be an amyloid beta sheet mimic, an antioxidant, molecular chaperone, or other agent. Exemplary agents for the treatment of amyloidosis are described in, e.g., WO/2008/141074. Exemplary molecular chaperones include, e.g., HSP60, HSP70, HSP90, HSP100, BiP, GRP94, GRP170, calnexin and calreticulin, Protein disulfide isomerase (PDI), Peptidyl prolyl cis-trans-isomerase (PPI), trimethylamine N-oxide (TMAO), betaine, glycine betaine, glycero-phosphorylcholine, carbohydrates such as, e.g., glycerol, sorbitol, arabitol, myo-inositol and trehalose, choline, 4-Phenyl butyric acid, and taurine-conjugated ursodeoxycholic acid.

The additional agent can be for treatment of chronic idiopathic pseudoobstruction. For example, the additional agent can be Prucalopride, Pyridostigmine, Metoclopramide, cisapride, linaclotide, octreotide, cannabinoids, and erythromycin.

The additional agent can be for treatment of dermatomyositis. For example, the additional agent can be Prednisolone, Methotrexate, Mycophenolate (CellCept/Myfortic), intravenous immunoglobulins, Azathioprine (Imuran), Cyclophosphamide, Rituximab, and Acthar Gel.

The additional agent can be for treatment of systemic lupus erytematosus. For example, the additional agent can be renal transplant, corticosteroids, immunosupressants, Hydroxychloroquine, Cyclophosphamide, Mycophenolic acid, immunosupressants, analgesics, intravenous immunoglobins, and the like.

The additional agent can be for treatment of anorexia and/or bulimia. For example, the additional agent can be olanzapine, a tricyclic antidepressant, an MAO inhibitor, mianserin, a selective serotonin reuptake inhibitor, e.g., fluoxetine, lithium carbonate, trazodone, and bupropion, phenytoin, carbamazepine, and valproic acid, opiate antagonists such as, e.g., naloxone and naltrexone, and topiramate.

The additional agent can be for treatment of depression. For example, the additional agent can be a selective serotonin reuptake inhibitor, a serotonin and norepinephrine reuptake inhibitor, bupropion, a tricyclic antidepressant, a monoamine oxidase inhibitor, and the like. The additional agent can be for treatment of paraneoplastic syndrome. The additional agent can be for treatment of a high cervical cord lesion. For example, the additional agent can be a corticosteroid or other anti-inflammatory medication. The additional agent can be for treatment of multiple sclerosis. For example, the additional agent can be interferon beta-1b, interferon beta-1a, Glatiramer acetate, Mitoxantrone, natalizumab, fingolimod, teriflunomide, or cladribine.

The additional therapeutic agent can be selected from the group consisting of serotonin agonists, serotonin antagonists, selective serotonin reuptake inhibitors, anticonvulsants, opioid receptor agonists, bradykinin receptor antagonists, NK receptor antagonists, adrenergic receptor agonists, benzodiazepines, gonadotropin-releasing hormone analogues, calcium channel blockers, and somatostatin analogs.

Dosages of the additional agent and of a compound described herein for use in the treatment of an enteric nervous system disorder can vary depending on the type of additional therapeutic agent employed, on the disease or condition being treated and so forth. Sub-therapeutic amounts of one or both of the additional agent and the compound can be used. The sub-therapeutic amount of one or both of the additional agent and the compound can be a synergistically effective amount. Therapeutically effective amounts of one or both of the additional agent and the compound can be used. The compound and the additional agent may be administered either simultaneously or sequentially. If administered sequentially, the attending physician or caretaker can decide on the appropriate sequence of administering the compound and the additional therapeutic agent.

In some embodiments, a method comprising administering any of the compounds described herein further comprises combination therapy with an additional therapeutic regimen. The additional therapeutic regimen can comprise implantation of a medical device. The medical device can be implanted in the stomach and/or abdomen, e.g., in the duodenum. The medical device can be an electrical device. The medical device can be a pacemaker. Such a pacemaker can utilize electrical current to induce stomach and/or duodenal contractions, thereby promoting gastrointestinal motility. Such medical devices, and methods of using them, are disclosed in U.S. Pat. No. 8,095,218, hereby incorporated by reference.

The invention is further described in detail by reference to the following examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Metopimazine and Metopimazine Acid are Selective and Potent Dopamine D2 Receptor Antagonists The pharmacological profile of metopimazine, metopimazine acid (MPZA), domperidone, and metoclopramide were assessed by radioligand binding and by a functional antagonist assay. For the radioligand binding assay, cell membranes of dopamine D2 receptor expressing cells were incubated with [3H]spiperone and competing drugs in buffer. The assay was terminated by rapid filtration, and the bound radioactive signal was determined by liquid scintillation counting. Results from the ligand binding assay are depicted in Table 1, below.

TABLE 1

| Pharmacological Profile. Radioligand Binding Affinity (Ki, nM) | | | | | | |
|---|---|---|---|---|---|---|
| | D2 | D3 | α1 | 5HT2 | 5HT3 | 5HT4 | H1 |
| Metopimazine (NG101) | 0.07 | 0.61 | 1.90 | 15.0 | Inactive | Inactive | 8.40 |

TABLE 1-continued

| Pharmacological Profile. Radioligand Binding Affinity (Ki, nM) | | | | | | | |
|---|---|---|---|---|---|---|---|
| | D2 | D3 | α1 | 5HT2 | 5HT3 | 5HT4 | H1 |
| Metopimazine-Acid (NG102) | 14.0 | >100 nM | 210 | 370 | Inactive | Inactive | 140 |
| Domperidone | 1.30 | 7.50 | | | | | |
| Metoclopramide | 64.0 | 16.0 | | | | | |

The functional antagonist assay was performed as described in Payne, S. L et al. (2002) J. Neurochem., 82: 1106-1117, hereby incorporated by reference. Specifically, [$^{35}$S]GTPγS binding assays were performed by incubating membranes from Dopaine D2 receptor expressing cells in a buffer supplemented with GDP and the drugs. After a defined pre-incubation period, [$^{35}$S]GTPγS was added to the reaction mixture. The assay was incubated and then terminated as described in the radioligand binding assay. Table 2 depicts results from the D2 functional antagonist assay.

TABLE 2

| Pharmacological profile: Dopamine D2 receptor antagonism. | | |
|---|---|---|
| Compounds | IC$_{50}$ (M) | K$_B$ (M) |
| Metopimazine | 2.2E−9 | 1.4E−10 |
| Metopimazine acid | 3.1E−7 | 2.1E−8 |
| Metoclopramide | 2.8E−7 | 1.9E−8 |
| Domperidone | 3.4E−9 | 2.3E−10 |
| Butaclamol (standard) | 6.4E−9 | 4.2E−10 |

These studies demonstrated for the first time that metopimazine and metopimazine-acid are potent and selective, D2 receptor antagonists. Furthermore, it was demonstrated that metopimazine and metopimazine acid act as peripherally restricted agents. Therapeutic plasma concentrations were 50-200 nM for metopimazine and 300-900 nM for metopimazine-acid.

Example 2: Metopimazine and Metopimazine Acid do not Interact with hERG Channels The ability of the compounds metopimazine, metopimazine acid, and domperidone to inhibit hERG channels was assessed. Briefly, hERG—expressing cultured cells incubated in various concentrations of the drugs were subjected to a voltage clamp assay. Cells were held at a −70 mV resting membrane potential. hERG currents were elicited with a single-pulse command voltage protocol using a depolarization to +40 mV. Elicited hERG currents were measured. Table 3, below, depicts experimental results from the study.

TABLE 3

| hERG Activity (% Inhibition of Tail Current) | | | |
|---|---|---|---|
| | 100 nM | 1 μM | 10 μM |
| Metopimazine (NG101) | 4.5 | 32 | 82 |
| Metopimazine-Acid (NG102) | 0.2 | 4 | 11 |
| Domperidone | 55 | 92 | 100 |

Results demonstrated that that the concentration necessary to inhibit 50% of the tail currents mediated by hERG channels was approximately 3 μM, >10 μM and 0.1 μM for metopimazine, metopimazine-acid and domperidone respectively. Metopimazine and metopimazine-acid were found to be 30 fold and >100 fold less potent, respectively, than domperidone to inhibit hERG channels.

Example 3: Metopimazine and Carbidopa Promote Gastric Motility in Canines

The effects of metopimazine and carbidopa on gastric motility in vivo were assessed using antral manometry in canines. Two healthy female hound dogs (24-28 kg) were involved in this study. Animals were fed an ad libitum chow diet (LabDiet®). After an overnight fast, the dogs were anesthetized with Pentothal (sodium thiopental, 11 mg/kg IV; Abbott Laboratories, North Chicago, Ill.) and maintained on 2-4% isoflurane (Abbott Laboratories) in oxygen (1 L/min) carrier gases delivered from a ventilator after endotracheal intubation. A cannula was placed in the jejunum 20 cm distal to the pylorus for the assessment of antral motility. Dogs were allowed to recover in their individual cages for 2 weeks. All experiments were performed after the dogs were completed recovered from the surgical procedure. The study was performed according to the National Institutes of Health Guidelines on the use of laboratory animals and approved by the Animal Care and Use Committee of the University of Texas Medical Branch at Galveston, Tex.

To investigate the effect of the drugs on antral manometry, the study of each drug dose was done on three randomized sessions on separate days following the consumption of one can of solid dog food: 1) a Control session: In which animals received the vehicle only; 2) Dose I session: in which the lower dose of the drug was used; and 3) Dose II session: in which the higher dose of the drug was used (please refer to table for drug doses). Drug administration was performed according to Table 4, below.

TABLE 4

| Drug administration protocol in canines | | | | | |
|---|---|---|---|---|---|
| | Drug | Dose 1 (mg/Kg) | Dose 2 (mg/Kg) | Vehicle | Route of administration | Timing |
| GM1 | metopimazine | 0.5 | 1 | water | Oral | 15 min prior to meal |
| GM2 | S-Carbidopa | 0.5 | 1 | DMSO 100 ml; then add water to attain volume | IV | 15 min prior to meal |
| GM3 | Dopamine hydrochloride | 50 mg/Dog | 100 mg/Dog | water | IV | Immediately before meal |

Antral manometry was performed as follows. Following an overnight fast, an intraluminal water-perfused manometry catheter was inserted into the antrum through the jejunal cannula. Antral manometry recording was initiated after the consumption of one can of solid food and continued for 3 hours. The catheter contained 3 manometric sensors at a 1 cm interval. Dogs were given 10 minutes of accommodation, prior to the start of the recording. For data analysis, motility index (MI), defined as the integrated area (area under curve—AUC) between baseline and contractions per hour, was calculated.

For statistical analysis, the Student's t-test was used for assessment of individual differences between groups (High dose, low dose of each drug) compared to control—Microsoft® Excel 2002). All values are expressed as mean±SEM. Significance was considered when p value was <0.05.

Figure 2:
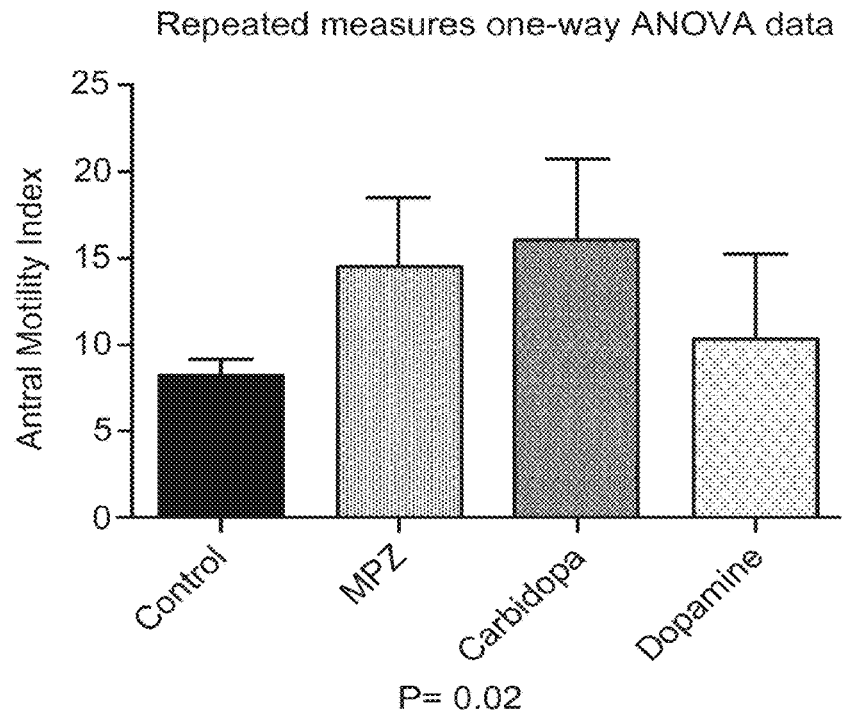
FIG. 2 depicts results from a gastric motility assay in canines treated with metopimazine, carbidopa, and dopamine.

Results are shown in FIG. 2. Results demonstrate that the 1 mg/kg of S-carbidopa robustly increased MI in all three of the channels tested (p=0.05). 1 mg/kg of metopimazine increased MI in all three channels as compared to the control or lower dose (p=0.06). By contrast, dopamine hydrochloride (50 mg/canine) decreased MI in all channels (p=0.06). Furthermore, no motor dysfunction was observed in canines administered metopimazine or carbidopa. These results indicate that metopimazine and carbidopa are both effective in enhancing gastric motility in vivo.

Example 4: Effect of Carbidopa on Gastric Emptying in Rodents

Animals:

Male Sprague-Dawley rats, purchased from the Charles River Lab, were housed in the animal facility of Veterans Research Education Foundation, which was maintained at 22~24° C., 55% relative humidity, with an automatic 12 h light/dark cycle. The animals received a standard laboratory rat chow and tap water ad libitum. The rats were around 400 g at 14 weeks age when used in gastric emptying study.

Drugs:

S-Carbidopa was purchased from Sigma (#: C1335). Stock solution of S-Carbidopa was prepared at 5 mg/ml using DMSO as solvent. 80 µl stock solution was further diluted into 1 ml distilled water to make 0.4 mg/ml. The effect of S-Carbidopa (1 mg/kg) on solid gastric emptying was studied.

Procedures:

Male SD rats were involved in this study. Rats were fasted in cages with metal wired mesh for 24 hours with free access to water; S-carbidopa (1 mg/kg) was administered to the rats by oral gavage. Control rats were not administered S-carbidopa. 15 minutes following administration, rats were given access to 2 g of rat chow pellets for ten minutes. All rats completely ingested the chow within the 10 minute time frame. Rats were sacrificed by sodium pentobarbital (100 mg/kg) overdose 90 min after feeding. The stomach was surgically isolated and removed. Gastric contents were recovered from the stomach, air dried for 48 hours and then weighed. Solid gastric emptying was calculated according to the following formula: Gastric emptying (%)=[1−(dried gastric content in g)/2 g]×100. All values are expressed as mean±SEM. Significance was considered when p value was <0.05.

Results:

Results from the rodent gastric emptying study are shown in Table 5 below. In 8 normal rats not administered carbidopa, the gastric emptying was 57.4±4.7%. All of the rats depicted in Table 5 were administered carbidopa.

TABLE 5

Effect of S-Carbidopa (1 mg/kg) on solid gastric emptying

| Rat ID | Group | body weight | Food given | stomach content | Gastric emptying (%) |
|---|---|---|---|---|---|
| 1 | 1 mg/Kg | 402 | 2 | 0.9 | 55 |
| 2 | 1 mg/Kg | 400 | 2 | 0.76 | 62 |
| 3 | 1 mg/Kg | 405 | 2 | 0.25 | 87.5 |
|  |  |  |  |  | 68.2 |

Initial results indicated that carbidopa improves solid gastric emptying in rats compared to that in control rats that were not administered carbidopa. Furthermore, no motor dysfunction was observed in subjects administered carbidopa.

Example 5: Effect of Metopimazine on Gastric Emptying in Rodents

Figure 3:
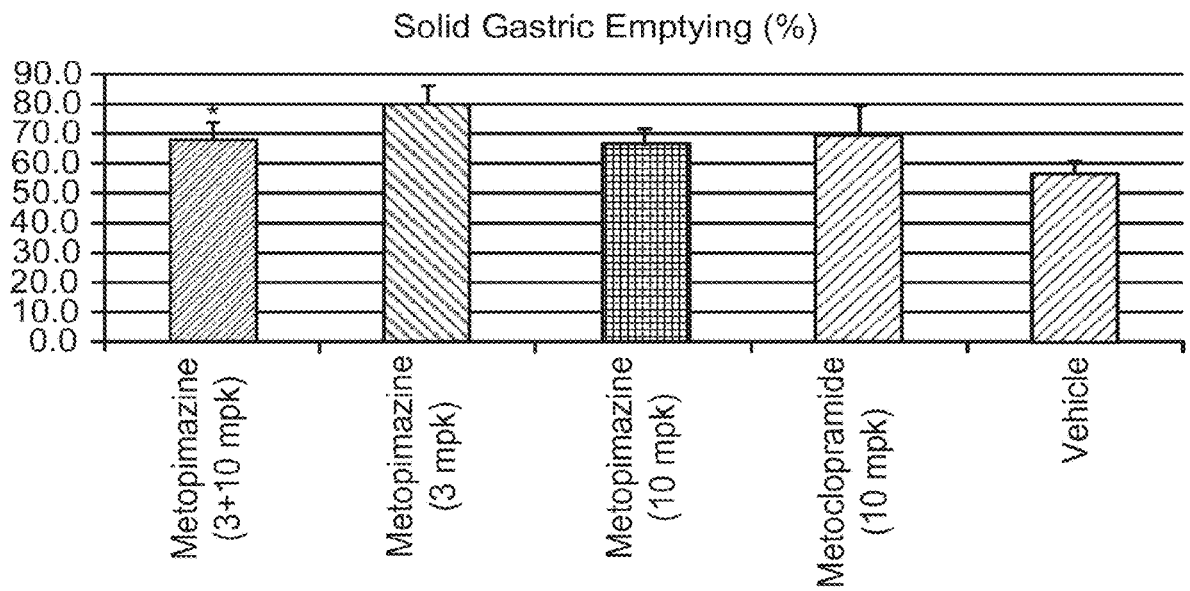
FIG. 3 depicts results from a gastric emptying assay in rodents treated with metopimazine and metoclopramide.

The effects of metopimazine (3 mg/kg and 10 mg/kg doses), metoclopramide (10 mg/kg), or vehicle administration on gastric emptying were assessed according to the protocol described in Example 4. Preliminary results are shown in FIG. 3, demonstrating that 3 mg/kg metopimazine increased gastric emptying by about 40% as compared to vehicle control, and that 10 mg/kg metopimazine increased gastric emptying by about 18% as compared to vehicle control. The overall effect of metopimazine (by pooling the 3 mg/kg and 10 mg/kg doses) was an increase in gastric emptying of about 20% as compared to vehicle control. These results indicate for the first time that metopimazine increases gastric emptying in vivo.

Example 6: Effect of Metopimazine, Metopimazine Acid on Cardiac Action Potentials in Vivo Effects of in vivo metopimazine, metopimazine acid, and carbidopa on canine cardiac action potentials are assessed by electrocardiography and telemetry.

Surgical Implantation of the Telemetry Device and ECG Leads.

Anesthesia is introduced to dogs. Balanced gaseous anesthesia is used throughout the surgical procedure. Once anesthetized, animals are shaved and surgically scrubbed, encompassing surgical sites of the right inguinal area, chest and right lateral abdomen. Throughout the surgical procedure, animals are monitored for continuous assessment of vital signs. An incision is made along the right medial thigh and the femoral artery exposed by blunt dissection. Another incision is made in the lateral lumbar area cranial to the iliac crest for a tunneling needle to be passed subcutaneously from the incision on the medial thigh to the lumbar incision. A blood pressure catheter is passed through the needle from the lumbar incision and the needle removed. The femoral artery is ligated distally and incised to insert a catheter that is advanced until the tip resided in the femoral artery/abdominal aorta. The catheter is then secured by ligation. The incision in the lumbar area is enlarged and a subcutaneous pocket created in the left dorsal lumbar area to hold the transmitter body. The transmitter (e.g., Data Sciences International, St Paul, Minn., USA) is inserted into the subcutaneous pocket and secured body. Electrocardiography (ECG) leads are positioned. The incision is closed. Postoperative recovery lasts, e.g., about 2 weeks during which supplemental analgesics/antibiotics are administered as needed. Once the postoperative recovery period is complete, the animal is examined for study acceptability by the staff veterinarian and the implanted transmitter signal verified.

Study Design.

Subjects are administered vehicle, metopimazine, metopimazine acid, carbidopa, or 0.3 mg/kg dofetilide (as a positive control) by oral gavage. ECGs, heart rate and arterial blood pressure data are recorded 1 hour prior to and then continuously for at least 6 hours following compound and/or vehicle administration. A blood sample for determination of compound plasma concentrations is collected from all subjects at approximately 6 h post-dose.

ECG Analysis.

An ECG waveform morphology assessment, for the entire monitoring period, is completed for each dog by, e.g., a safety pharmacologist or veterinarian cardiologist. Standard ECG intervals (PR, RR, QRS and QT) are automatically measured by the data acquisition system and reported as, e.g., 10 min averages. The signals are collected with Data Sciences International Systems hardware. PR and QT manual overreads are conducted as appropriate. The manual measurements are completed from 50 mm $s^{-1}$ tracings at 30 min intervals. A mean of the three waveforms per time point are reported. QT intervals are corrected for heart rate ($QT_c$) values by, e.g., using the formula by Funck-Bretano and Jaillon (1993).

Statistical Analysis.

The systemic blood pressures and heart rate data radiotelemetry are averaged across consecutive 10 min time intervals during the 6 h post-dosing period for each animal. A baseline of a stable 10 min period is selected prior to the start of dosing. The baseline measurement for each animal is subtracted on each dosing day from the animal's post-dosing 10 min averages. Dose-level averages (and accompanying standard deviation (s.d.) of these baseline-adjusted 10 min averages are calculated across study animals. ANOVA (e.g., repeated measures ANOVA) are applied to these baseline-adjusted averages. Pairwise t-tests are applied within the ANOVA to identify the presence of significant differences of the dose levels relative to vehicle. These t-tests are performed at a 0.05/2=0.025 significance level, so that the overall error rate across the comparisons in a given interval are not higher than 0.05. ECG interval data (reported at 30 min intervals) are analyzed using, e.g., repeated-measures ANOVA techniques similar to the systemic blood pressure and heart rate data described above.

$QT_c$ intervals are increased in dogs administered dofetilide throughout the post-dose period of 1-6 hours. Dofetilide administration also increases the incidence of premature ventricular contractions, T-wave abnormalities, and right bundle branch block. By contrast, no significant increases in $QT_c$ intervals are found in dogs administered metopimazine, metopimazine acid, or carbidopa, as compared to vehicle-administered animals.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating gastroparesis in a subject in need thereof, comprising administering to the subject a pharmaceutical composition comprising a pharmaceutically acceptable salt of metopimazine,

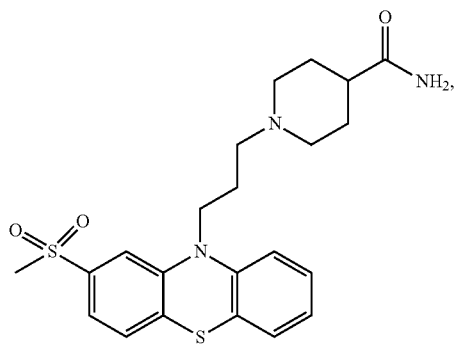 [SMILES: CS(=O)(=O)c1ccc2c(c1)N(CCCN1CCC(C(N)=O)CC1)c1ccccc1S2]

and a pharmaceutically acceptable carrier.

2. The method of claim 1, wherein the gastroparesis comprises a symptom selected from the group consisting of nausea, vomiting, delayed gastric emptying, diarrhea, abdominal pain, gas, bloating, gastroesophageal reflux, reduced appetite, and constipation.

3. The method of claim 2, wherein the gastroparesis comprises the symptom nausea.

4. The method of claim 2, wherein the gastroparesis comprises the symptom vomiting.

5. The method of claim 1, wherein the pharmaceutical composition is administered chronically.

6. The method of claim 1, wherein the pharmaceutical composition is administered acutely.

7. The method of claim 1, wherein the pharmaceutical composition is administered for at least 6 days.

8. The method of claim 7, wherein the pharmaceutical composition is administered for at least 7 days.

9. The method of claim 7, wherein the pharmaceutical composition is administered for at least four weeks.

10. The method of claim 7, Wherein the pharmaceutical composition is administered for at least 12 weeks.

11. The method of claim 1, wherein the pharmaceutical composition is administered one time per day.

12. The method of claim 1, wherein the pharmaceutical composition is administered two times per day.

13. The method of claim 1, wherein the pharmaceutical composition is administered one to four times per day.

14. The method of claim 1, wherein the pharmaceutical composition is administered four times per day.

15. The method of claim 1, Wherein more than 20 mg of the pharmaceutically acceptable salt of metopimazine is administered per day.

* * * * *